United States Patent
Casta et al.

(10) Patent No.: US 9,651,549 B2
(45) Date of Patent: *May 16, 2017

(54) LATERAL FLOW ASSAYS USING DNA DENDRIMERS

(71) Applicant: Genisphere, LLC, Hatfield, PA (US)

(72) Inventors: Louis J. Casta, Philadelphia, PA (US); James M. Kadushin, Gilbertsville, PA (US); Lori A. Getts, Huntingdon Valley, PA (US); Robert C. Getts, Collegeville, PA (US)

(73) Assignee: Genisphere, LLC, Hatfield, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/844,601

(22) Filed: Mar. 15, 2013

(65) Prior Publication Data

US 2014/0017704 A1 Jan. 16, 2014

Related U.S. Application Data

(60) Provisional application No. 61/671,662, filed on Jul. 13, 2012.

(51) Int. Cl.
*G01N 33/76* (2006.01)
*G01N 33/548* (2006.01)
*G01N 33/558* (2006.01)
*C12Q 1/68* (2006.01)

(52) U.S. Cl.
CPC ......... *G01N 33/548* (2013.01); *C12Q 1/6813* (2013.01); *G01N 33/558* (2013.01); *G01N 33/76* (2013.01)

(58) Field of Classification Search
CPC .... G01N 33/548; G01N 33/558; G01N 33/76; C12Q 1/6813
See application file for complete search history.

(56) References Cited

U.S. PATENT DOCUMENTS

| | | |
|---|---|---|
| 3,641,235 A | 2/1972 | Weiss |
| 3,959,078 A | 5/1976 | Guire |
| 3,966,897 A | 6/1976 | Renn et al. |
| 4,094,647 A | 6/1978 | Deutsch et al. |
| 4,168,146 A | 9/1979 | Grubb et al. |
| 4,299,916 A | 11/1981 | Litman et al. |
| 4,347,312 A | 8/1982 | Brown et al. |
| 4,366,241 A | 12/1982 | Tom et al. |
| 4,391,904 A | 7/1983 | Litman et al. |
| 4,425,438 A | 1/1984 | Bauman et al. |
| 4,517,288 A | 5/1985 | Giegel et al. |
| 4,639,425 A * | 1/1987 | Baier ............ 436/518 |
| 4,695,554 A | 9/1987 | O'Connell et al. |
| 4,703,017 A | 10/1987 | Campbell et al. |
| 4,743,560 A | 5/1988 | Campbell et al. |
| 4,857,453 A | 8/1989 | Ullman et al. |
| 4,956,302 A | 9/1990 | Gordon et al. |
| 4,960,691 A | 10/1990 | Gordon et al. |
| 5,073,484 A | 12/1991 | Swanson et al. |
| 5,075,078 A | 12/1991 | Osikowicz et al. |
| 5,120,643 A | 6/1992 | Ching et al. |
| 5,141,875 A | 8/1992 | Kelton et al. |
| 5,175,270 A | 12/1992 | Nilsen et al. |
| 5,252,496 A | 10/1993 | Kang et al. |
| 5,275,785 A | 1/1994 | May et al. |
| 5,484,904 A | 1/1996 | Nilsen et al. |
| 5,487,973 A | 1/1996 | Nilsen et al. |
| 5,504,013 A | 4/1996 | Senior |
| 5,514,602 A | 5/1996 | Brooks, Jr. et al. |
| 5,591,645 A | 1/1997 | Rosenstein |
| 5,602,040 A | 2/1997 | May et al. |
| 5,656,448 A | 8/1997 | Kang et al. |
| 5,712,170 A | 1/1998 | Kouvonen et al. |
| 5,846,737 A | 12/1998 | Kang |
| 6,017,767 A | 1/2000 | Chandler |
| 6,046,038 A | 4/2000 | Nilsen |
| 6,072,043 A | 6/2000 | Nilsen |
| 6,110,687 A | 8/2000 | Nilsen |
| 6,117,631 A | 9/2000 | Nilsen |
| 6,156,271 A | 12/2000 | May |
| 6,187,269 B1 | 2/2001 | Lancesseur et al. |
| 6,187,598 B1 | 2/2001 | May et al. |
| 6,274,723 B1 | 8/2001 | Nilsen |
| 6,319,676 B1 | 11/2001 | Nazareth et al. |
| 6,352,862 B1 | 3/2002 | Davis et al. |
| 6,399,398 B1 | 6/2002 | Cunningham et al. |
| 6,485,982 B1 | 11/2002 | Charlton |

(Continued)

FOREIGN PATENT DOCUMENTS

| | | |
|---|---|---|
| EP | 0149168 | 7/1985 |
| EP | 0250137 | 12/1987 |

(Continued)

OTHER PUBLICATIONS

Genisphere, An introduction to 3DNA™ technology, pp. 1-4, 2005, retrieved from http://genisphere.com/sites/default/files/pdf/3DNAtechnology_05_05.pdf on Jan. 29, 2014.*
Broach et al., "High throughput screening for drug discovery," Nature (1996) 384:14-16.
Burbaum et al., "New technologies for high-throughput screening," Curr Opin Chem Biol (1997) 1:72-78.
Fernandes, "Letter from the society president," J. Biomol. Screening (1997) 2:1.
International Search Report and Written Opinion for PCT/US2013/050401, mailed Sep. 18, 2013, 12 pages.
Janzen et al., "High throughput screening as a discovery tool in the pharmaceutical industry," Lab Robotics Automation (1996) 8:261-265.
Kanehisa, "Use of statistical criteria for screening potential homologies in nucleic acid sequences," Nucleic Acids Res. (1984) 12:203-213.
Seal et al., "Point-of-care nucleic acid lateral-flow tests," IVD Technology (2006), retrieved from the Internet Oct. 29, 2013, 11 pages.
Slide presentation entitled "Enhancement of sensitivity in lateral flow immunoassays with Genisphere's 3DNA Dendrimer Technology," publicly disclosed on Jul. 16, 2012, 28 pages.

(Continued)

*Primary Examiner* — Andrea S Grossman
(74) *Attorney, Agent, or Firm* — Stradley Ronon Stevens & Young LLP

(57) ABSTRACT

The present invention relates to novel lateral flow devices using DNA dendrimers, and the methods for detecting an analyte using the lateral flow devices.

8 Claims, 12 Drawing Sheets

(56) References Cited

U.S. PATENT DOCUMENTS

| | | | |
|---|---|---|---|
| 6,656,744 B2 * | 12/2003 | Pronovost et al. | 436/514 |
| RE38,430 E | 2/2004 | Rosenstein | |
| 6,770,487 B2 | 8/2004 | Crosby | |
| 7,144,742 B2 * | 12/2006 | Boehringer et al. | 436/514 |
| 7,175,992 B2 | 2/2007 | Fong | |
| 7,189,522 B2 | 3/2007 | Esfandiari | |
| RE39,664 E | 5/2007 | Gordon et al. | |
| 7,238,538 B2 | 7/2007 | Freitag et al. | |
| 7,258,837 B2 * | 8/2007 | Yager et al. | 422/417 |
| 7,317,532 B2 | 1/2008 | Sharrock et al. | |
| 7,879,597 B2 | 2/2011 | Esfandiari | |
| 2010/0112725 A1 * | 5/2010 | Babu et al. | 436/518 |
| 2010/0190179 A1 | 7/2010 | Nilsen | |
| 2011/0160090 A1 | 6/2011 | Cary | |
| 2013/0171740 A1 | 7/2013 | Sakakibara | |

FOREIGN PATENT DOCUMENTS

| | | | |
|---|---|---|---|
| EP | 0323605 | 7/1989 | |
| EP | 586590 B1 * | 7/1999 | C12Q 1/00 |
| EP | 1319179 B1 * | 3/2008 | G01N 33/53 |
| GB | 1526708 | 9/1978 | |
| JP | 2001/503517 | 3/2001 | |
| JP | 2001/512034 | 8/2001 | |
| WO | WO 9010716 A1 * | 9/1990 | |
| WO | WO-9818488 | 5/1998 | |
| WO | WO-9906595 | 2/1999 | |
| WO | WO-99/40438 | 8/1999 | |
| WO | WO 03033735 A2 * | 4/2003 | C12Q 1/68 |
| WO | WO-2006/098804 | 9/2006 | |
| WO | WO-2006/099191 | 9/2006 | |
| WO | WO-2009/137055 | 11/2009 | |
| WO | WO-2010/017544 | 2/2010 | |
| WO | WO-2011/103074 | 8/2011 | |
| WO | WO-2012/032794 | 3/2012 | |

OTHER PUBLICATIONS

Slide entitled "3DNA Dendrimer Technology," publicly disclosed prior to Jul. 13, 2012, 1 page.
Slide entitled "Lateral flow hcG protein detection by 3DNA Dendrimers (direct sandwich method)," publicly disclosed on Jul. 16, 2012, 1 page.
Technical note entitled "Adaptation of 3DNA Dendrimers to point of care assays," publicly disclosed on Jul. 16, 2012, 4 pages.
Technical note (revised) entitled "Adaptation of 3DNA Dendrimers to point of care assays," publicly disclosed on Jul. 16, 2012, 4 pages.
Literature entitled "UltraAmp Signal Amplifiers," publicly disclosed prior to Jul. 13, 2012, 6 pages.
Communication pursuant to Rules 161(1) and 162 EPC for EP 13740178.2, mailed Feb. 20, 2015, 2 pages.
International Preliminary Report on Patentability for PCT/US2013/050401, mailed Jan. 22, 2015, 8 pages.
Non-final Office Action dated Nov. 10, 2016 in U.S. Appl. No. 14/414,699.
Non-final Office Action dated Mar. 10, 2016 in U.S. Appl. No. 14/414,699.

* cited by examiner

LATERAL FLOW ASSAYS USING DNA DENDRIMERS

CROSS REFERENCES TO RELATED APPLICATIONS

This application claims the priority benefit of U.S. provisional application Ser. No. 61/671,662, filed Jul. 13, 2012. The content of the above-referenced application is incorporated by reference in its entirety.

TECHNICAL FIELD

The present invention relates to novel lateral flow devices using DNA dendrimers, and the methods for detecting an analyte using the lateral flow devices.

BACKGROUND OF THE INVENTION

The 3DNA® DNA dendrimer is a proprietary dendritic molecule comprised solely of DNA. As a class, dendrimers are complex, highly branched molecules built from interconnected natural or synthetic monomeric subunits. A DNA dendrimer is constructed from DNA monomers, each of which is made from two DNA strands that share a region of sequence complementarity located in the central portion of each strand (FIG. 1). Monomers are combined during the manufacturing process to prepare DNA dendrimers of different sizes and shapes (FIG. 2). In order to prevent DNA dendrimers from "falling apart" over time, chemical "spot welds" are sometimes added to the growing assembly during the process using UV light via the intercalation and activation of psoralen cross-linkers. Dendrimers have been historically purified according to their size and molecular weight on denaturing sucrose gradients after ultracentrifugation.

DNA dendrimers have previously been used in membrane based assays, specifically for the detection of nucleic acids and proteins non-covalently immobilized to various membrane substrates, including nitrocellulose and nylon. These assays typically required the use of dendrimers specifically derivatized to contain targeting or binding moieties specific for the target analyte, and typically required several hours to overnight for optimal binding. Improvement of sensitivity from signal amplification ranged from 5 to 500 fold over the non-dendrimer version of the assay.

DNA dendrimers have also been shown to be useful as signal amplifiers in a number of other applications, including nucleic acid (DNA/RNA) microarrays, ELISAs, ELOSAs, bead based immunoassays, protein arrays and other similar assays. These assays are all characterized by the immobilization of the analyte or target material to a substrate either directly via a non-covalent or a covalent binding process, or indirectly via the binding to a previously immobilized ligand, which generally required several steps prior to or during the assay process. DNA dendrimers containing up to hundreds of label moieties would then bind either directly or indirectly to the analyte via a targeting device which would simultaneously directly bind to both the analyte (or indirectly to a ligand bound to the analyte) and the dendrimer, thereby creating a bridge between the multi-labeled dendrimer and the analyte. Signal was generated in these assays either directly from label moieties on the dendrimer (e.g. fluorescent dyes) or indirectly via the binding of signaling moieties to binding sites on the dendrimer (e.g. streptavidin-HRP binding to dendrimer bound biotins).

Therefore, there is a need for devices and methods that overcome the limitations of the current technologies and methodologies, especially for more sensitive lateral flow assays. The present invention addresses these and other related needs.

BRIEF SUMMARY OF THE INVENTION

In one aspect, the present disclosure provides for a test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a detectable label and a DNA dendrimer, said DNA dendrimer comprises a first component that links said DNA dendrimer to a binding reagent linkable to said DNA dendrimer, an analyte linkable to said DNA dendrimer, or an analyte analog linkable to said DNA dendrimer, and a second component that links said DNA dendrimer to said detectable label linkable to said DNA dendrimer.

In some embodiments, the analyte is not a polynucleotide; or the DNA dendrimer comprises from about 1 to about 324, preferably from about 60 to about 324, from about 80 to about 300 or from about 100 to about 200, the first components; or the DNA dendrimer, before the test device is used, is dried on a location on the test device upstream from the test zone. In some embodiments, the test reagent or binding reagent specifically binds to an analyte.

In another aspect, the present disclosure provides for a method for detecting an analyte in a liquid sample, which method comprises: a) contacting a liquid sample with the above test device, wherein the liquid sample is applied to a site of the test device upstream of the test zone; b) transporting an analyte, if present in the liquid sample, a detectable label and a DNA dendrimer to the test zone; and c) assessing the presence, absence, and/or amount of a signal generated by the detectable label at the test zone to determine the presence, absence and/or amount of the analyte in the liquid sample.

In still another aspect, the present disclosure provides for a test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a DNA dendrimer linked to a detectable label non-covalently, and said DNA dendrimer comprises a component that links said DNA dendrimer to a binding reagent linkable to said DNA dendrimer, an analyte linkable to said DNA dendrimer, or an analyte analog linkable to said DNA dendrimer.

In some embodiments, the analyte is not a polynucleotide; or the DNA dendrimer comprises from about 1 to about 324, preferably from about 60 to about 324, from about 80 to about 300 or from about 100 to about 200, the first components; or the DNA dendrimer, before the test device is used, is dried on a location on the test device upstream from the test zone. In some embodiments, the test reagent or binding reagent specifically binds to an analyte.

In yet another aspect, the present disclosure provides for a method for detecting an analyte in a liquid sample, which method comprises: a) contacting a liquid sample with the above test device, wherein the liquid sample is applied to a site of the test device upstream of the test zone; b) transporting an analyte, if present in the liquid sample, a detectable label and a DNA dendrimer to the test zone; and c) assessing the presence, absence, and/or amount of a signal generated by the detectable label at the test zone to determine the presence, absence and/or amount of the analyte in the liquid sample.

The principles of the present test devices and methods can be applied, or can be adapted to apply, to the lateral flow test devices and assays known in the art. For example, the principles of the present test devices and methods can be applied, or can be adapted to apply, to the lateral flow test devices and assays disclosed and/or claimed in the U.S. Pat. Nos. 3,641,235, 3,959,078, 3,966,897, 4,094,647, 4,168,146, 4,299,916, 4,347,312, 4,366,241, 4,391,904, 4,425,438, 4,517,288, 4,960,691, 5,141,875, 4,857,453, 5,073,484, 4,695,554, 4,703,017, 4,743,560, 5,075,078, 5,591,645, 5,656,448, RE 38,430 E, 5,602,040, 6,017,767, 6,319,676, 6,352,862, 6,485,982, 5,120,643, 4,956,302, RE 39,664 E, 5,252,496, 5,514,602, 7,238,538 B2, 7,175,992 B2, 6,770,487 B2, 5,712,170, 5,275,785, 5,504,013, 6,156,271, 6,187,269, 6,399,398, 7,317,532, EP 0,149,168 A1, EP 0,323,605 A1, EP 0,250,137 A2, GB 1,526,708 and WO99/40438.

DETAILED DESCRIPTION OF THE INVENTION

Figure 1:
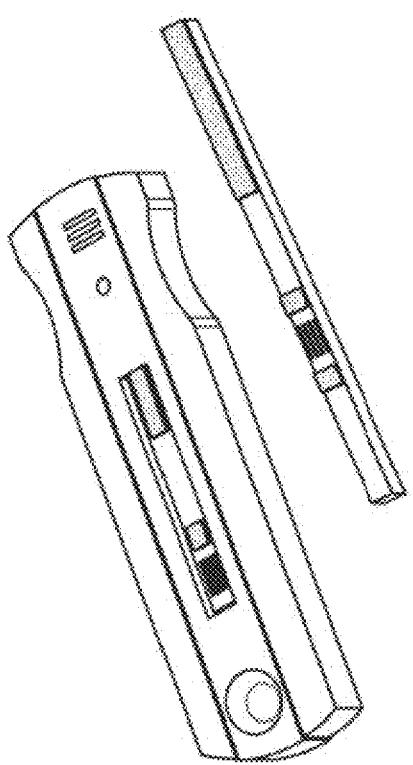
FIG. 1 illustrates an exemplary, standard lateral flow "point of care" assay format.
Figure 1:
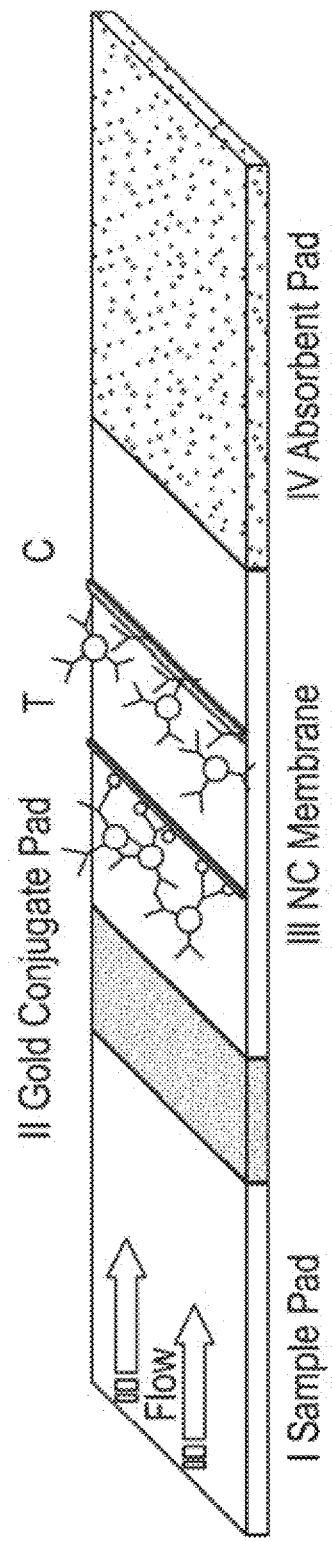

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "binding reagent" refers to any substance that binds to target or analyte with desired affinity and/or specificity. Non-limiting examples of the binding reagent include cells, cellular organelles, viruses, particles, microparticles, molecules, or an aggregate or complex thereof, or an aggregate or complex of molecules. Exemplary binding reagents can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid, an aptamer and a complex thereof.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included within the definition. As used herein, the term encompasses not only intact polyclonal or monoclonal antibodies, but also fragments thereof (such as Fab, Fab', F(ab')2, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "specifically binds" refers to the specificity of a binding reagent, e.g., an antibody, such that it preferentially binds to a defined analyte or target. Recognition by a binding reagent or an antibody of a particular analyte or target in the presence of other potential interfering substance(s) is one characteristic of such binding. In some embodiments, a binding reagent that specifically binds to an analyte avoids binding to other interfering moiety or moieties in the sample to be tested.

As used herein the term "avoids binding" refers to the specificity of particular binding reagents, e.g., antibodies or antibody fragments. Binding reagents, antibodies or antibody fragments that avoid binding to a particular moiety generally contain a specificity such that a large percentage of the particular moiety would not be bound by such binding reagents, antibodies or antibody fragments. This percentage generally lies within the acceptable cross reactivity percentage with interfering moieties of assays utilizing the binding reagents or antibodies directed to detecting a specific target. Frequently, the binding reagents, antibodies or antibody fragments of the present disclosure avoid binding greater than about 90% of an interfering moiety, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, binding reagents, antibodies or antibody fragments of the present disclosure avoid binding greater than about 70%, or greater than about 75%, or greater than about 80%, or greater than about 85% of an interfering moiety.

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein the term "isolated" refers to material removed from its original environment, and is altered from its natural state. For example, an isolated polypeptide could be coupled to a carrier, and still be "isolated" because that polypeptide is not in its original environment.

As used herein, high-throughput screening (HTS) refers to processes that test a large number of samples, such as samples of diverse chemical structures against disease targets to identify "hits" (see, e.g., Broach, et al., High throughput screening for drug discovery, *Nature,* 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72-78 (1997)). HTS operations are highly automated and computerized to handle sample preparation, assay procedures and the subsequent processing of large volumes of data.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The terms "polynucleotide," "oligonucleotide," "nucleic acid" and "nucleic acid molecule" are used interchangeably herein to refer to a polymeric form of nucleotides of any length, e.g., at least 8, 9, 10, 20, 30, 40, 50, 100, 200, 300, 400, 500, 1,000 or more nucleotides, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucleic Acids Res.* 12:203-215.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. Also included are soil and water samples and other environmental samples, viruses, bacteria, fungi, algae, protozoa and components thereof.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

B. Lateral Assay Devices Using DNA Dendrimers

In one aspect, the present disclosure provides for a test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a detectable label and a DNA dendrimer, said DNA dendrimer comprises a first component that links said DNA dendrimer to a binding reagent linkable to said DNA dendrimer, an analyte linkable to said DNA dendrimer, or an analyte analog linkable to said DNA dendrimer, and a second component that links said DNA dendrimer to said detectable label linkable to said DNA dendrimer.

In some embodiments, the analyte is not a polynucleotide; or the DNA dendrimer comprises from about 1 to about 324, preferably from about 60 to about 324, from about 80 to about 300 or from about 100 to about 200, the first components; or the DNA dendrimer, before the test device is used, is dried on a location on the test device upstream from the test zone. In some embodiments, the test reagent or binding reagent specifically binds to an analyte.

The first component and the second component can be any suitable substances. For example, the first component and/or the second component can be an inorganic molecule or moiety, an organic molecule or moiety, or a complex thereof. Exemplary organic molecules or moieties include an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

In some embodiments, the first component and the second component are the same. In other embodiments, the first component and the second component are different. In still other embodiments, one of the first component and the second component is a polynucleotide and the other is a non-polynucleotide moiety. In yet other embodiments, the first component is a polynucleotide and the second component is a non-polynucleotide moiety, e.g., a polypeptide.

The DNA dendrimer can be linked to any suitable binding reagent via the first component. For example, the first component can link the DNA dendrimer to a binding reagent that binds to an analyte, preferably a binding reagent that specifically binds to an analyte. In another example, the first component can link the DNA dendrimer to a binding reagent that binds to another binding reagent that binds to an analyte, preferably a binding reagent that specifically binds to an analyte.

The DNA dendrimer can be linked to any suitable reagent via the second component. For example, the second component can link the DNA dendrimer to a detectable label. In another example, the second component can link the DNA dendrimer to another binding reagent that is linked to a detectable label.

The present devices can be used in any suitable assay formats, e.g., sandwich or competitive assay formats. In some embodiments, the test device is to be used in a sandwich assay for the analyte and wherein the test reagent at the test zone binds, and preferably specifically binds, to the analyte, a second binding reagent that binds, and preferably specifically binds, to the analyte is used, the second binding reagent comprises a polynucleotide that is substantially complementary to a polynucleotide that is the first component of a DNA dendrimer. In other embodiments, the test device is to be used in a sandwich assay for the analyte and wherein the test reagent at the test zone binds, and preferably specifically binds, to the analyte, a second binding reagent that binds to another binding reagent that binds, and preferably specifically binds, to an analyte is used, the second binding reagent comprises a polynucleotide that is substantially complementary to a polynucleotide that is the first component of a DNA dendrimer.

In still other embodiments, the test device is to be used in a competitive assay for the analyte and wherein the test reagent at the test zone is an analyte or an analyte analog, a second binding reagent that binds, and preferably specifically binds, to the analyte is used, the second binding reagent comprises a polynucleotide that is substantially complementary to a polynucleotide that is the first component of a DNA dendrimer, and the analyte or an analyte analog at the test zone competes with an analyte in the sample for binding to the second binding reagent. In yet other embodiments, the test device is to be used in a competitive assay for the analyte and wherein the test reagent at the test zone is an analyte or an analyte analog, a second binding reagent that binds to another binding reagent that binds, and preferably specifically binds, to an analyte is used, the second binding reagent comprises a polynucleotide that is substantially complementary to a polynucleotide that is the first component of a DNA dendrimer, and the analyte or an analyte analog at the test zone competes with an analyte in the sample for binding to the binding reagent that is bound to the second binding reagent.

The analytes and the various reagents used in connection with the present devices, e.g., analyte, analyte analog, test reagent and/or binding reagent, can be any suitable substances. In some embodiments, the analyte, analyte analog, test reagent and/or binding reagent is an inorganic molecule, an organic molecule or a complex thereof. Exemplary organic molecules include an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

In other embodiments, the analyte is a polypeptide, a small molecule or an antigen, and the test reagent and/or binding reagent that binds to the analyte is an antibody that binds, and preferably specifically binds, to the polypeptide, small molecule or an antigen. In still other embodiments, the analyte is a polynucleotide, and the test reagent and/or binding reagent that binds to the analyte is another polynucleotide that is substantially complementary to the analyte polynucleotide. In yet other embodiments, the analyte is a polynucleotide, and the test reagent and/or binding reagent that binds to the analyte is a non-polynucleotide moiety, e.g., a polypeptide, an antibody or a receptor that binds to the analyte polynucleotide.

The matrix can comprise or be made of any suitable material. In some embodiments, the matrix comprises nitrocellulose, glass fiber, polypropylene, polyethylene (preferably of very high molecular weight), polyvinylidene flouride, ethylene vinylacetate, acrylonitrile and/or polytetrafluoro-ethylene. See e.g., U.S. Pat. No. 6,187,598. It can be advantageous to pre-treat the membrane with a surface-active agent during manufacture, as this can reduce any inherent hydrophobicity in the membrane and therefore enhance its ability to take up and deliver a moist sample rapidly and efficiently. The matrix can also be made from paper or other cellulosic materials. In some embodiments, the matrix comprises or is made of nitrocellulose or glass fiber.

The matrix can also be in any suitable form or shape. In some embodiments, the matrix is in the form a strip or a circle. The matrix can also comprise or be made of any suitable number of element. In some embodiments, the matrix is a single element or comprises multiple elements.

The present test devices can comprise any suitable additional elements. In some embodiments, the test device can further comprise a sample application element upstream from and in fluid communication with the matrix. In other embodiments, the test device can further comprise a liquid absorption element downstream from and in fluid communication with the matrix. In still other embodiments, the test device can further comprise a control zone comprising means for indicating proper flow of the liquid sample and/or a valid test result. In yet other embodiments, at least a portion of the matrix is supported by a solid backing. In yet other embodiments, the entire matrix is supported by a solid backing.

The various reagents used in connection with the present devices, e.g., the DNA dendrimer, the various binding reagents and/or the detectable, can be dried on the test devices before use. In some embodiments, a substance is dried on a portion of the matrix upstream from the test zone, the dried substance being capable of being moved by a liquid sample and/or a further liquid to the test zone and/or a control zone to generate a detectable signal, the dried substance being at least one of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer.

In other embodiments, two substances are dried on a portion of the matrix upstream from the test zone, the dried substances being capable of being moved by a liquid sample and/or a further liquid to the test zone and/or a control zone to generate a detectable signal, the dried substances being at least two of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the label linkable to the DNA dendrimer; the dried substances, whether separately or in complex, being capable of being moved by a liquid sample and/or a further liquid to the test zone and/or a control zone to generate a detectable signal.

In still other embodiments, three substances are dried on a portion of the matrix upstream from the test zone, the dried substances being capable of being moved by a liquid sample and/or a further liquid to the test zone and/or a control zone to generate a detectable signal, the dried substances being all of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the label linkable to the DNA dendrimer.

The above substance(s) can be dried on any suitable location of the test devices. In some embodiments, the substance(s) is dried on a conjugate element that is upstream from the test zone. In other embodiments, the substance(s) is located downstream from a sample application place on the test device. In still other embodiments, the substance(s) is located upstream from a sample application place on the test device.

Any suitable detectable label can be used in connection with the present test devices. In some embodiments, the detectable label is a soluble label, e.g., a soluble enzyme or fluorescent label. In other embodiments, the detectable label is a particle label. The particle label can be a visible or a non-visible particle label. In some embodiments, the visible particle label is selected from the group consisting of a gold particle, a latex particle, a Q-Dot, a carbon nanotube, a silver particle and a silver coated particle. In some embodiments, the non-visible particle label is a fluorescent particle. A detectable label can also be a moiety that effects a change in mass and/or charge. A DNA dendrimer can effect a change in mass and/or charge. In some embodiments, a detectable label can be a DNA dendrimer, e.g., the DNA dendrimer itself or an additional DNA dendrimer.

In some embodiments, the substance(s) is dried in the presence of a material that: a) stabilizes the dried substance(s); b) facilitates solubilization or resuspension of the dried substance(s) in a liquid; and/or c) facilitates mobility of the dried substance(s). Any suitable material can be used. For example, the material can be a protein, a peptide, a polysaccharide, a sugar, a polymer, a gelatin and a detergent. See e.g., U.S. Pat. Nos. 5,120,643 and 6,187,598.

In some embodiments, a sample liquid alone is used to transport the analyte and/or the substance(s) to the test zone. In other embodiments, a developing liquid is used to transport the analyte and/or the substance(s) to the test zone.

The test device can further comprise a housing that covers at least a portion of the test device, wherein the housing comprises a sample application port to allow sample application upstream from or to the test zone and an optic opening around the test zone to allow signal detection at the test zone and/or the control zone. In some embodiments, the housing covers the entire test device. In other embodiments, at least a portion of the sample receiving portion of the matrix or the sample application element is not covered by the housing and a sample is applied to the portion of the sample receiving portion of the matrix or the sample application element outside the housing and then transported to the test zone.

The DNA dendrimer, the various binding reagents and the detectable label can be linked in any suitable manner, e.g., non-covalently linked or covalently linked. In some embodiments, none of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; is covalently crosslinked to each other.

In other embodiments, at least two of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are covalently crosslinked to each other.

In still other embodiments, all of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are covalently crosslinked to each other.

Any suitable DNA dendrimer can be used. For example, the DNA dendrimers disclosed and/or claimed in the U.S. Pat. Nos. 5,175,270, 5,487,973, 6,046,038, 6,072,043, 6,110,687, 6,117,631 and 6,274,723 can be used. The DNA dendrimers can comprise any suitable number of second components that link the DNA dendrimer to a detectable label. In some embodiments, the DNA dendrimer comprises from about 10 to about 1,500, preferably from about 40 to about 1,500, from about 100 to about 1,400, from about 500 to about 1,200, or from about 900 to about 1,100, second components that link the DNA dendrimer to a detectable label linkable to the DNA dendrimer. The label can be the same or can be different.

The DNA dendrimers can comprise any suitable number of DNA nucleotides. In some embodiments, the DNA dendrimer comprises from about 400 to about 80,000, preferably from about 4,000 to about 80,000, from about 10,000 to about 80,000, from about 30,000 to about 80,000, or from about 60,000 to about 80,000, DNA nucleotides.

The DNA dendrimers can comprise any suitable number of layers. In some embodiments, the DNA dendrimer comprises a one-layer, a two-layer, a three-layer or a four-layer structure.

In some embodiments, the present disclosure provides for a test device for detecting an analyte in a liquid sample wherein the liquid sample has moved laterally along the test device to generate a detectable signal at the test zone.

C. Methods for Detecting an Analyte in a Liquid Sample

In another aspect, the present disclosure provides for a method for detecting an analyte in a liquid sample, which method comprises: a) contacting a liquid sample with the test device described in the above Section B, wherein the liquid sample is applied to a site of the test device upstream of the test zone; b) transporting an analyte, if present in the liquid sample, a detectable label and a DNA dendrimer to the test zone; and c) assessing the presence, absence, and/or amount of a signal generated by the detectable label at the test zone to determine the presence, absence and/or amount of the analyte in the liquid sample.

The present methods can be used in any suitable assay formats. For example, the DNA dendrimer, the various binding reagents and/or the detectable label can be premixed with a sample liquid and/or developing liquid, and then the mixture is applied to the test device to initiate an assay. Alternatively, one or more of the DNA dendrimer, the various binding reagents and/or the detectable label can be dried on a suitable location of the test device, and a sample liquid and/or developing liquid is applied to the test device to initiate an assay.

In some embodiments, the liquid sample and at least one of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are premixed to form a mixture and the mixture is applied to the test device.

In other embodiments, the liquid sample and at least two of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are premixed to form a mixture and the mixture is applied to the test device.

In still other embodiments, the liquid sample and all of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are premixed to form a mixture and the mixture is applied to the test device.

The present methods can be conducted in a liquid comprising a surfactant or detergent, e.g., Tween-20. In some embodiments, the method is conducted in a liquid comprising from about 0.001% (v/v) to about 5% (v/v), preferably, from about 0.01% (v/v) to about 0.5% (v/v), or at about 0.01% (v/v) or less Tween-20. The present methods can also be conducted in a liquid comprising a polymer, e.g., dextran sulfate. In some embodiments, the method is conducted in a liquid comprising from about 0.1% (v/v) to about 5% (v/v), preferably from about 0.5% (v/v) to about 1% (v/v), dextran sulfate.

In some embodiments, a substance is dried on a portion of the test device upstream from the test zone, the dried substance is solubilized or resuspended, and transported to the test zone and/or a control zone to generate a detectable signal, the dried substance being at least one of: 1) the DNA dendrimer; 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer.

The substance can be dried on any suitable location of the test device. In some embodiments, the dried substance is located downstream from the sample application site, and the dried substance is solubilized or resuspended, and transported to the test zone and/or a control zone by the liquid sample. In other embodiments, the dried substance is located upstream from the sample application site, and the dried substance is solubilized or resuspended, and transported to the test zone and/or a control zone by another liquid. In still other embodiments, the dried substance is solubilized or resuspended, and transported to the test zone and/or a control zone by the liquid sample alone. In yet other embodiments, the analyte and/or dried substance is solubilized or resuspended, and transported to the test zone and/or a control zone by another liquid.

The present methods can be used to assess an analyte in any suitable sample. In some embodiments, the present methods can be used to assess an analyte in a body fluid sample, e.g., a whole blood, a serum, a plasma and a urine sample. In other embodiments, the present methods can be used to assess an analyte in a sample derived from a biological, a forensics, a food, a biowarfare, or an environmental source.

The present methods can be used for any suitable purpose. In some embodiments, the present methods can be used to quantify or semi-quantify the amount of an analyte in a liquid sample. In other embodiments, the present methods can be used to detect multiple analytes in a liquid sample. In still other embodiments, the present methods can be used to quantify or semi-quantify the amounts of the multiple analytes in the liquid sample.

The present methods can be used to assess any suitable analyte. In some embodiments, the present methods can be used to assess an analyte selected from the group consisting of a cell, a virus and a molecule.

In some embodiments, the present methods are automated and/or are used in high throughput format.

D. Lateral Assay Devices Using DNA Dendrimer Linked to a Detectable Label Non-Covalently In still another aspect, the present disclosure provides for a test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a DNA dendrimer linked to a detectable label non-covalently, and said DNA dendrimer comprises a component that links said DNA dendrimer to a binding reagent linkable to said DNA dendrimer, an analyte linkable to said DNA dendrimer, or an analyte analog linkable to said DNA dendrimer.

In some embodiments, the analyte is not a polynucleotide; or the DNA dendrimer comprises from about 1 to about 324, preferably from about 60 to about 324, from about 80 to about 300 or from about 100 to about 200, the first components; or the DNA dendrimer, before the test device is used, is dried on a location on the test device upstream from the test zone. In some embodiments, the test reagent or binding reagent specifically binds to an analyte.

The component can be any suitable substance. For example, the component can be an inorganic molecule or moiety, an organic molecule or moiety, or a complex thereof. Exemplary organic molecules or moieties include an amino acid, a peptide, a protein, a nucleoside, a nucleotide, an oligonucleotide, a nucleic acid, a vitamin, a monosaccharide, an oligosaccharide, a carbohydrate, a lipid and a complex thereof. In some embodiments, the component is a polynucleotide.

The present devices can be used in any suitable assay formats, e.g., sandwich or competitive assay formats. In some embodiments, the test device is to be used in a sandwich assay for the analyte and wherein the test reagent at the test zone binds, preferably specifically binds, to the analyte, a second binding reagent that binds, preferably specifically binds, to the analyte is used, the second binding reagent comprises a polynucleotide that is substantially complementary to a polynucleotide that is the component of a DNA dendrimer. In other embodiments, the test device is to be used in a sandwich assay for the analyte and wherein the test reagent at the test zone binds, preferably specifically binds, to the analyte, a second binding reagent that binds to another binding reagent that binds, preferably specifically binds, to an analyte is used, the second binding reagent comprises a polynucleotide that is substantially complementary to a polynucleotide that is the component of a DNA dendrimer.

In still other embodiments, the test device is to be used in a competitive assay for the analyte and wherein the test reagent at the test zone is an analyte or an analyte analog, a second binding reagent that binds, preferably specifically binds, to the analyte is used, the second binding reagent comprises a polynucleotide that is substantially complementary to a polynucleotide that is the component of a DNA dendrimer, and the analyte or an analyte analog at the test zone competes with an analyte in the sample for binding to the second binding reagent. In yet other embodiments, the test device is to be used in a competitive assay for the analyte and wherein the test reagent at the test zone is an analyte or an analyte analog, a second binding reagent that binds to another binding reagent that binds, preferably specifically binds, to an analyte is used, the second binding reagent comprises a polynucleotide that is substantially complementary to a polynucleotide that is the component of a DNA dendrimer, and the analyte or an analyte analog at the test zone competes with an analyte in the sample for binding to the binding reagent that is bound to the second binding reagent.

The analytes and the various reagents used in connection with the present devices, e.g., analyte, analyte analog, test reagent and/or binding reagent, can be any suitable substances. In some embodiments, the analyte, analyte analog, test reagent and/or binding reagent is an inorganic molecule, an organic molecule or a complex thereof. Exemplary organic molecule can be an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

In other embodiments, the analyte is a polypeptide, a small molecule or an antigen, and the test reagent and/or binding reagent that binds to the analyte is an antibody that binds, preferably specifically binds, to the polypeptide, small molecule or antigen. In still other embodiments, the analyte is a polynucleotide, and the test reagent and/or binding reagent that binds to the analyte is another polynucleotide that is substantially complementary to the analyte polynucleotide. In yet other embodiments, the analyte is a polynucleotide, and the test reagent and/or binding reagent that binds to the analyte is a non-polynucleotide moiety, e.g., a polypeptide, an antibody or a receptor that binds to the analyte polynucleotide.

The matrix can comprise or be made of any suitable material. In some embodiments, the matrix comprises nitrocellulose, glass fiber, polypropylene, polyethylene (preferably of very high molecular weight), polyvinylidene flouride, ethylene vinylacetate, acrylonitrile and/or polytetrafluoro-ethylene. See e.g., U.S. Pat. No. 6,187,598. It can be advantageous to pre-treat the membrane with a surface-active agent during manufacture, as this can reduce any inherent hydrophobicity in the membrane and therefore enhance its ability to take up and deliver a moist sample rapidly and efficiently. The matrix can also be made from paper or other cellulosic materials. In some embodiments, the matrix comprises or is made of nitrocellulose or glass fiber.

The matrix can also be in any suitable form or shape. In some embodiments, the matrix is in the form a strip or a circle. The matrix can also comprise or be made of any suitable number of element. In some embodiments, the matrix is a single element or comprises multiple elements.

The present test devices can comprise any suitable additional elements. In some embodiments, the test device can further comprise a sample application element upstream from and in fluid communication with the matrix. In other embodiments, the test device can further comprise a liquid absorption element downstream from and in fluid communication with the matrix. In still other embodiments, the test device can further comprise a control zone comprising means for indicating proper flow of the liquid sample and/or a valid test result. In yet other embodiments, at least a portion of the matrix is supported by a solid backing. In yet other embodiments, the entire matrix is supported by a solid backing.

The various reagents used in connection with the present devices, e.g., the DNA dendrimer and/or the various binding reagents, can be dried on the test devices before use. In some embodiments, a substance is dried on a portion of the matrix upstream from the test zone, the dried substance being capable of being moved by a liquid sample and/or a further liquid to the test zone and/or a control zone to generate a detectable signal, the dried substance being at least one of: 1) the DNA dendrimer; and 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer. In other embodiments, both of the DNA dendrimer, and the first binding reagent that binds to the analyte, the second binding reagent that binds to another binding reagent that binds to the analyte, the analyte or the analyte analog, are dried on a portion of the matrix upstream from the test zone.

The substance(s) can be dried on any suitable location of the test device. In some embodiments, the substance(s) is dried on a conjugate element that is upstream from the test zone. In other embodiments, the substance(s) is located downstream from a sample application place on the test device. In still other embodiments, the substance(s) is located upstream from a sample application place on the test device.

Any suitable detectable label can be used in connection with the present test devices. In some embodiments, the detectable label is a soluble label, e.g., a soluble enzyme or fluorescent label. In other embodiments, the detectable label is a particle label. The particle label can be a visible or a non-visible particle label. In some embodiments, the visible particle label is selected from the group consisting of a gold particle, a latex particle, a Q-Dot, a carbon nanotube, a silver particle and a silver coated particle. In some embodiments, the non-visible particle label is a fluorescent particle. A detectable label can also be a moiety that effects a change in mass and/or charge. A DNA dendrimer can effect a change in mass and/or charge. In some embodiments, a detectable label can be a DNA dendrimer, e.g., the DNA dendrimer itself or an additional DNA dendrimer.

In some embodiments, the substance(s) is dried in the presence of a material that: a) stabilizes the dried substance(s); b) facilitates solubilization or resuspension of the dried substance(s) in a liquid; and/or c) facilitates mobility of the dried substance(s). Any suitable material can be used. For example, the material can be a protein, a peptide, a polysaccharide, a sugar, a polymer, a gelatin and a detergent. See e.g., U.S. Pat. Nos. 5,120,643 and 6,187,598.

In some embodiments, a sample liquid alone is used to transport the analyte and/or the substance(s) to the test zone. In other embodiments, a developing liquid is used to transport the analyte and/or the substance(s) to the test zone.

The test device can further comprise a housing. In some embodiments, the test device further comprise a housing that covers at least a portion of the test device, wherein the housing comprises a sample application port to allow sample application upstream from or to the test zone and an optic opening around the test zone to allow signal detection at the test zone and/or the control zone. In other embodiments, the housing covers the entire test device. In still other embodiments, at least a portion of the sample receiving portion of the matrix or the sample application element is not covered by the housing and a sample is applied to the portion of the sample receiving portion of the matrix or the sample application element outside the housing and then transported to the test zone.

Any suitable DNA dendrimer can be used. For example, the DNA dendrimers disclosed and/or claimed in the U.S. Pat. Nos. 5,175,270, 5,487,973, 6,046,038, 6,072,043, 6,110,687, 6,117,631 and 6,274,723 can be used. The DNA dendrimers can comprise any suitable number of components that link the DNA dendrimer to a binding reagent linkable to said DNA dendrimer. In some embodiments, the DNA dendrimer comprises from about 1 to about 324, preferably from about 60 to about 324, from about 80 to about 300 or from about 100 to about 200, components that link the DNA dendrimer to a binding reagent linkable to said DNA dendrimer.

The DNA dendrimers can comprise any suitable number of the detectable label. In some embodiments, the DNA dendrimers comprises from about 10 to about 1,500, preferably from about 40 to about 1,500, or from about 100 to about 1,200, or from about 900 to about 1,100, the detectable labels. The label can be the same or can be different.

The DNA dendrimers can comprise any suitable number of DNA nucleotides. In some embodiments, the DNA dendrimer comprises from about 400 to about 80,000, preferably from about 4,000 to about 80,000, from about 10,000 to about 80,000, from about 30,000 to about 80,000, or from about 60,000 to about 80,000, DNA nucleotides.

The DNA dendrimers can comprise any suitable number of layers. In some embodiments, the DNA dendrimer comprises a one-layer, a two-layer, a three-layer or a four-layer structure.

In some embodiments, the present disclosure provides for a test device wherein the liquid sample has moved laterally along the test device to generate a detectable signal at the test zone.

E. Methods for Detecting an Analyte in a Liquid Sample

In yet another aspect, the present disclosure provides for a method for detecting an analyte in a liquid sample, which method comprises: a) contacting a liquid sample with the test device described in the above Section D, wherein the liquid sample is applied to a site of the test device upstream of the test zone; b) transporting an analyte, if present in the liquid sample, a detectable label and a DNA dendrimer to the test zone; and c) assessing the presence, absence, and/or amount of a signal generated by the detectable label at the test zone to determine the presence, absence and/or amount of the analyte in the liquid sample.

The present methods can be used in any suitable assay formats. For example, the DNA dendrimer and/or the various binding reagents can be premixed with a sample liquid and/or developing liquid, and then the mixture is applied to the test device to initiate an assay. Alternatively, the DNA dendrimer and/or the various binding reagents can be dried on a suitable location of the test device, and a sample liquid and/or developing liquid is applied to the test device to initiate an assay.

In some embodiments, the liquid sample and at least one of: 1) the DNA dendrimer linked to a detectable label non-covalently; and 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; are premixed to form a mixture and the mixture is applied to the test device.

In other embodiments, the liquid sample and both of: 1) the DNA dendrimer linked to a detectable label non-covalently; and 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; are premixed to form a mixture and the mixture is applied to the test device.

The present methods can be conducted in a liquid comprising a surfactant or detergent, e.g., Tween-20. In some embodiments, the method is conducted in a liquid comprising from about 0.001% (v/v) to about 5% (v/v), preferably, from about 0.01% (v/v) to about 0.5% (v/v), or at about 0.01% (v/v) or less Tween-20. The present methods can also be conducted in a liquid comprising a polymer, e.g., dextran sulfate. In some embodiments, the method is conducted in a liquid comprising from about 0.1% (v/v) to about 5% (v/v), preferably from about 0.5% (v/v) to about 1% (v/v), dextran sulfate.

In some embodiments, a substance is dried on a portion of the test device upstream from the test zone, the dried substance is capable of being moved by a liquid sample and/or a further liquid to the test zone and/or a control zone to generate a detectable signal, the dried substance being at least one of: 1) the DNA dendrimer linked to a detectable label non-covalently; and 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer.

The substance can be dried on any suitable location of the test device. In some embodiments, the dried substance is located downstream from the sample application site, and the dried substance is solubilized or resuspended, and transported to the test zone and/or a control zone by the liquid sample. In other embodiments, the dried substance is located upstream from the sample application site, and the dried substance is solubilized or resuspended, and transported to the test zone and/or a control zone by another liquid. In still other embodiments, the dried substance is solubilized or resuspended, and transported to the test zone and/or a control zone by the liquid sample alone. In yet other embodiments, the analyte and/or dried substance is solubilized or resuspended, and transported to the test zone and/or a control zone by another liquid.

The present methods can be used to assess an analyte in any suitable sample. In some embodiments, the present methods can be used to assess an analyte in a body fluid sample, e.g., a whole blood, a serum, a plasma and a urine sample. In other embodiments, the present methods can be used to assess an analyte in a sample derived from a biological, a forensics, a food, a biowarfare, or an environmental source.

The present methods can be used for any suitable purpose. In some embodiments, the present methods can be used to quantify or semi-quantify the amount of an analyte in a liquid sample. In other embodiments, the present methods can be used to detect multiple analytes in a liquid sample. In still other embodiments, the present methods can be used to quantify or semi-quantify the amounts of the multiple analytes in the liquid sample.

The present methods can be used to assess any suitable analyte. In some embodiments, the present methods can be used to assess an analyte selected from the group consisting of a cell, a virus and a molecule.

In some embodiments, the present methods are automated and/or are used in high throughput format.

F. Exemplary Embodiments

In exemplary embodiments, this disclosure describes the use of DNA dendrimers as signal amplification devices in "point-of-care" (POC) detection assays, typified as immunoassays that require little skill by the end-user, provide simple readouts and results interpretation, and are performed in a relatively short period of time with minimal procedural steps. Typically, POC tests include a variety of assay formats utilizing a variety of different signaling strategies incorporating visible and non-visible signaling devices, including several types of immunochromatographic assays (visible readout lateral flow, dual path platform, etc.), fluorescent, electrochemical and enzymatic detection assays using membranes and lateral flow type devices, and assays which incorporate the use of microfluidics and biosensors (with or without membranes or paper substrates). These assays may be capable of detecting a different single analyte or multiple analytes simultaneously. Commonly, POC tests are mostly represented by lateral flow immunoassays, which usually include a membrane strip which contain an immobilized ligand (antibody or antigen) in a "test" line on the membrane which is capable of binding to the analyte of interest and indicates the presence of the analyte in a test sample when the test line is positive. Lateral flow assays also often contain a "control" line which indicates that the assay has worked appropriately. Other components of a lateral flow assay include a sample pad where the analyte containing sample is added to the strip assay, a conjugate pad which contains dried down assay reagents, a membrane (typically nitrocellulose) capable of capillary action and the site of the immunological reaction between the immobilized ligand, the analyte and the signal generating ligand and related devices, and a wicking pad on the distal end of the membrane which serves to draw liquid via capillary action in the membrane from the sample pad, through the membrane, and into the wicking pad. When liquid sample is added to the sample pad, the liquid flows from the sample pad into the conjugate pad, where any signal generating reagents previously dried into the conjugate pad (e.g., gold particle conjugated with anti-analyte antibody) are re-hydrated and are carried with the sample liquid front into the membrane. The analyte and signal generating reagents then react with the test line (T) and control line (C), and a positive result of detection of the analyte is indicated by a signal at the test line. The wick or absorbent pad at the distal end of the membrane serves to "pull" the liquid through the membrane via capillary actions (see FIG. 1).

Figure 2:
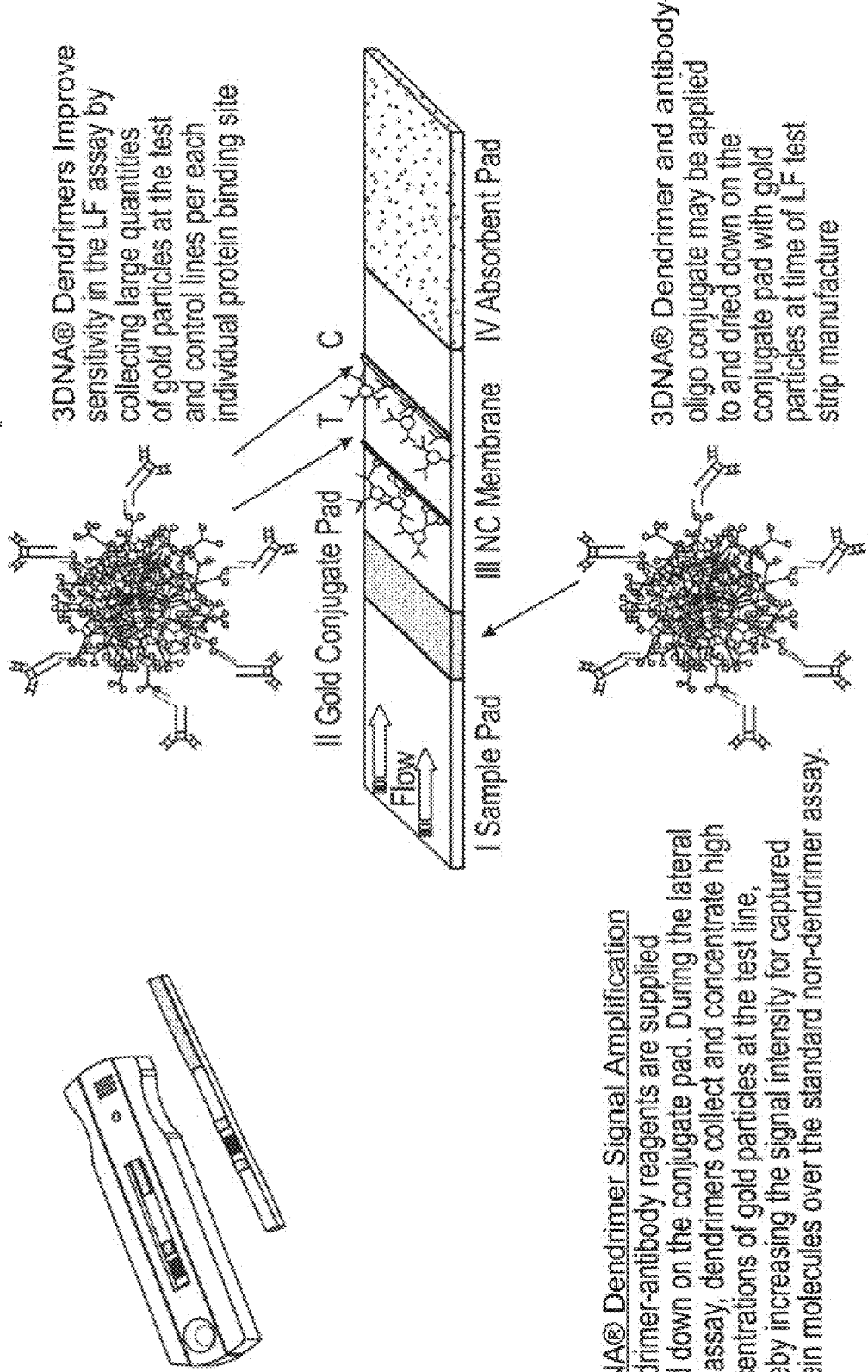
FIG. 2 illustrates an exemplary dendrimer enhanced lateral flow "point of care" assay format. Dendrimer-antibody reagents are supplied dried down on the conjugate pad. During the lateral flow assay, dendrimers collect and concentrate high concentrations of gold particles at the test line, thereby increasing the signal intensity for captured protein molecules over the standard non-dendrimer assay.

The use of DNA dendrimers in lateral flow and other POC assays has only recently been explored (see e.g., U.S. patent application US 2011/0160090 A1), even though these applications were similar in concept to other immunoassays already incorporating DNA dendrimers as signal amplifiers (e.g., ELISA). Previously, it was assumed by the inventors that DNA dendrimers would likely not be suitable for use in lateral flow assays given the nature and size of the dendrimers and prior experiences of poor performance of the dendrimers in other membrane based assays (e.g. Western blot immunoassays), which included low signal amplification and very high non-specific background. Notwithstanding this assumption, and given the ability of the DNA dendrimer to deliver hundreds of label moieties to a single binding site (compared to a single or at most 5-10 labels using non-dendrimer lateral flow reagents), we decided to perform lateral flow assays utilizing DNA dendrimers as signal amplifiers. Specifically, DNA dendrimers containing nearly 1,000 biotin moieties per dendrimer were synthesized and tested in a model lateral flow hCG assay, with an anti-hCG antibody-oligonucleotide conjugate serving as the "bridge" reagent between the hCG analyte and a streptavidin-gold conjugate serving as the signal generator (the streptavidin-gold binding the biotins on the dendrimers). A standard hCG assay utilizing gold particles conjugated with anti-hCG antibody was also performed (FIG. 2). To our surprise, the lateral flow assay with the DNA dendrimers performed extremely well, providing up to 128 fold of improvement of sensitivity over the standard hCG assay, with little or no non-specific background signal across the assay membrane. Note it was not expected that DNA dendrimers would perform well in lateral flow assays as we expected the dendrimers would not be able to efficiently perfuse the membrane during the performance of a lateral flow assay due to the size and highly branched structure of the dendrimer. Further, the non-specific binding of signal generating moieties in DNA dendrimer lateral flow assays does occur but is controllable via blocking and buffer selection activities.

Specific Applications of DNA Dendrimers in Lateral Flow POC Assays

DNA dendrimers can be used in POC lateral flow protein detection assays in sandwich and/or competitive assay formats. In some embodiments, the DNA dendrimers are used in a direct sandwich assay. This assay format requires the immobilization of a first antibody specific for the analyte, typically as an antibody stripe line located on a membrane strip capable of drawing liquid from one end to another of the membrane via capillary action. An aqueous sample containing the analyte is added to the end of membrane strip and the analyte is captured by the immobilized first antibody. A second antibody specific for the analyte (but directed to a different epitope than the first immobilized antibody) and conjugated to an oligonucleotide (the "antibody-oligo conjugate") is allowed to bind to the analyte. The antibody-oligo conjugate is either separate from or previously bound to a DNA dendrimer containing labeling moieties capable of generating signal or binding signaling devices. The DNA dendrimer is bound to the antibody-oligo conjugate and generates signal located on the test line located on the membrane strip. Visible signal is typically generated by binding gold particles to the label moieties on the DNA dendrimer (e.g. streptavidin-gold particles binding to DNA dendrimer-bound biotin moieties) or by label moieties bound to the DNA dendrimer capable of generating signal directly (e.g. fluorescent dyes). An example of this method would include an antibody-oligo conjugate that contains an antibody that binds directly to an analyte such as human chorionic gonadotropin (hCG), thereby forming a direct link between the antibody-oligo conjugate and the immobilized analyte. Generally, the higher the signal, the more positive the result.

In some embodiments, the DNA dendrimers are used in an indirect sandwich assay. This format is very similar to the "direct sandwich assay" except that the antibody-oligo conjugate contains an antibody that does not bind directly to the analyte, but rather binds to another component that in turns binds to the analyte. An example of this method would include an antibody-oligo conjugate that contains an antibody that binds to another antibody which in turn binds directly to an analyte such as human chorionic gonadotropin (hCG), thereby forming an indirect link between the antibody-oligo conjugate and the immobilized analyte. Generally, the higher the signal, the more positive the result.

In some embodiments, the DNA dendrimers are used in a direct competitive assay. This assay format generally incorporates the use of immobilized analyte (rather than a first antibody) which then binds to an antibody-oligo conjugate, a DNA dendrimer and a label generating moiety. When analyte-containing sample is added, soluble antibody-oligo conjugate is bound to soluble analyte, which competes for the binding of the antibody-oligo conjugate to the immobilized analyte, thereby causing a result of lower signal (or no signal). An example of this method would include an antibody-oligo conjugate that contains an antibody that binds directly to an analyte such as human chorionic gonadotropin (hCG), thereby forming a direct link between the antibody-oligo conjugate and the soluble analyte, and which competes for the binding of the antibody-oligo conjugate, DNA dendrimer and signal generating moieties to the immobilized hCG analyte. Generally, the lower the signal, the more positive the result.

In some embodiments, the DNA dendrimers are used in an indirect competitive assay. This format is very similar to the "direct competitive assay" except that the antibody-oligo conjugate contains an antibody that does not bind directly to the analyte, but rather binds to another component that in turns binds to the analyte. An example of this method would include an antibody-oligo conjugate that contains an antibody that binds to another antibody which in turn binds directly to an analyte such as human chorionic gonadotropin (hCG), thereby forming an indirect link between the antibody-oligo conjugate and the soluble hCG analyte. Generally, the lower the signal, the more positive the result.

Further, DNA dendrimers are used in POC nucleic acid detection assays. In some embodiments, the DNA dendrimers are used in a direct detection of immobilized nucleic acid target. This assay would include the immobilization of a nucleic acid probe onto a POC device, which in turn would hybridize to a first nucleic acid sequence located in a nucleic acid molecule of interest in a sample, which in turn would be directly bound by a DNA dendrimer containing a nucleic acid probe targeting device capable of hybridizing to a second nucleic acid sequence located in the aforementioned nucleic acid molecule of interest in a sample. Signal may be generated in this assay as previously described for the protein detection assays. An example of this method would include an immobilized DNA probe specific for a cystic fibrosis (CF) mutation hybridizing to the specifically PCR amplified DNA amplicon containing the partial gene sequence for the CF gene and mutation of interest, further hybridized to the DNA dendrimer-bound DNA oligonucleotide specific for the CF gene (but to another portion of the sequence which will not interfere with the binding of the immobilized probe), thereby forming a direct link between the DNA dendrimer and the immobilized hybridized CF amplicon. Generally, the higher the signal, the more positive the result.

In some embodiments, the DNA dendrimers are used in an indirect detection of immobilized target. This assay is similar to the "direct detection of immobilized nucleic acid target", except that the DNA dendrimer is indirectly bound to the immobilized nucleic acid molecule of interest. Indirect binding may be via a nucleic acid molecule, or via other means, such as binding to a hapten contained within a device in turn bound to the immobilized nucleic acid molecule of interest. An example of this method would include an immobilized DNA probe specific for a cystic fibrosis (CF)

mutation hybridizing to the specifically PCR amplified DNA amplicon containing the partial gene sequence for the CF gene and mutation of interest, further hybridized to a second soluble DNA probe specific for another portion of the CF amplicon and containing a biotin on its 5 prime (5') end, and a DNA dendrimer containing an anti-biotin antibody-oligo conjugate, thereby forming an indirect link between the DNA dendrimer and the immobilized hybridized CF amplicon. Generally, the higher the signal, the more positive the result.

In some embodiments, the DNA dendrimers are used in a competitive nucleic acid POC assays. As discussed above for protein assays, competitive POC nucleic acid detection assays, both direct and indirect, are possible, based on the premise that the labeled moiety (DNA dendrimer or labeled device bound to DNA dendrimer) will bind to soluble analyte and will compete for the binding to immobilized ligand. Generally, the lower the signal, the more positive the result.

In exemplary embodiments, several novel aspects relate to the use of the DNA dendrimer in the above POC assays. In some embodiments, the improvement of sensitivity when using DNA dendrimers in POC assays was not directly proportional to the number of label moieties bound to the dendrimer, with the sensitivity improvement less than would otherwise be predicted and in a non-linear manner when increasing the number of label moieties from 240 to 480 to 960 labels per dendrimer, while keeping the number of targeting devices constant. Further, there was no improvement or a slight loss of sensitivity when using a dendrimer with 1,440 labels per dendrimer. Conversely, sensitivity was significantly improved by increasing the number of targeting devices on the dendrimer, which we believe improved the probability of binding (or collision) between the DNA dendrimer and the targeted analyte, either via direct or indirect binding between said DNA dendrimer and analyte.

In some embodiments, the DNA dendrimers (with and/or without related assay reagents) are "dried down" onto the POC test during the manufacture of the POC test components, thereby reducing the number of steps required to perform the POC assay. Typically, assay reagents, including antibody-gold particle conjugates, are dried down onto a conjugate pad for POC lateral flow test strips to reduce the number of steps required to perform the assay. The dried down reagent(s) are rehydrated via the addition of the aqueous test sample or by the addition of aqueous buffers added to the dehydrated reagent(s) during the assay procedure, eliminating the need to add these reagents as aqueous preparations during the performance of the assay. To the inventors' knowledge, DNA dendrimers and antibody-oligo conjugates had not been dried down in any assay format, and it was unknown whether dried dendrimers and antibody-oligo conjugates would perform appropriately after rehydration. We have clearly demonstrated that DNA dendrimer and antibody-oligo conjugates can be dried down onto a POC lateral flow test strip using manufacturing methods similar to those used for other lateral flow reagents, and the dendrimer and antibody-oligo conjugates perform as well as or better than reagents used in a non-dried down liquid state.

In some embodiments, the ability to vary the number of steps in a POC assay using dried down DNA dendrimers is combined with some or all of the assay components. Prior POC lateral flow methods include one-step and multi-step assays which incorporate reagents that are either all dried down onto the lateral flow test strip, or contain some reagents which are dried down and others which are not dried down but are used as a liquid reagent during the assay. These reagents include but are not limited to the DNA dendrimer, antibody-oligo conjugate, gold particle conjugate capable of binding to the DNA dendrimer, native antibody specific for the analyte (for an indirect lateral flow assay), and other buffers and blockers as required for performing the assay. We have also found that the DNA dendrimer may be dried down onto the lateral flow test strip in combination with all the other reagent components required for the test, resulting in a one-step process. Further, we have found that one or more of the aforementioned reagent components may be used singly or in combination as components in a POC lateral flow assay, resulting in a method that may require two, three or more steps to perform.

In some embodiments, DNA dendrimers are used with ancillary labeled particles, including gold and latex particles, and various bridging strategies are utilized for binding signaling particles to the dendrimers. DNA dendrimers have been adapted for use with various types of particles that impart a visible or non-visible signal to POC assays. For visible POC lateral flow assays, the use of gold particles capable of binding to moieties incorporated into the structure of the DNA dendrimer has been demonstrated. For example, gold particles containing surface immobilized streptavidin or anti-biotin antibody are used to bind to DNA dendrimers containing incorporated biotin moieties. Further, gold or other types of particles containing immobilized nucleic acid probes have been used to bind to complementary nucleic acid sequences on DNA dendrimers. Additionally, other types of particles, including latex particles, Q-Dots, carbon nanotubes, silver particles or silver coated particles, and others may be used for visible signal generation when capable of binding to DNA dendrimers. DNA dendrimer binding particles may also be used for generating non-visible signals, for example Q-Dots and latex particles containing fluorescent dyes for fluorescent assays.

In some embodiments, the DNA dendrimers are directly labeled with signaling moieties (and signal generating moieties such as enzymes), thereby avoiding the use of signal generating particles, where such dendrimer-label complexes are fully soluble in aqueous and other solutions. There are clear advantages for using soluble DNA dendrimers in POC assays, including the reduction of steps achieved by avoiding the use of an insoluble signal generating particles, the inherent stability of the soluble DNA dendrimer either in liquid form or in a dehydrated form as compared to particle conjugates, the ease and efficiency of re-hydration of the DNA dendrimer after being dried to a POC assay substrate, and others.

In some embodiments, the DNA dendrimers used in POC assays are manufactured in a manner which eliminates the need for covalent crosslinking of label moieties and targeting devices to the DNA dendrimer as required for other previously disclosed DNA dendrimer assay applications. Typically, in other assay formats including the use of DNA dendrimers on DNA and protein microarrays, DNA dendrimers have had label moieties and targeting devices covalently crosslinked and have been ultimately purified using a relatively inefficient sucrose gradient centrifugation purification method previously disclosed (See e.g., U.S. Pat. Nos. 5,175,270 and 5,487,973). We have empirically determined that DNA dendrimers which have not been crosslinked after the addition of label moieties or targeting devices perform as well as DNA dendrimers prepared in the customary manufacturing process. This was a surprising finding which will significantly reduce the cost of producing said DNA dendrimers for use in a variety of POC lateral flow assay formats.

The present invention is further illustrated by the following exemplary embodiments:

1. A test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a detectable label and a DNA dendrimer, said DNA dendrimer comprises a first component that links said DNA dendrimer to a binding reagent linkable to said DNA dendrimer, an analyte linkable to said DNA dendrimer, or an analyte analog linkable to said DNA dendrimer, and a second component that links said DNA dendrimer to said detectable label linkable to said DNA dendrimer, and wherein:

a) said analyte is not a polynucleotide; or b) said DNA dendrimer comprises from about 1 to about 324, preferably from about 60 to about 324, from about 80 to about 300 or from about 100 to about 200, said first components; or c) said DNA dendrimer, before said test device is used, is dried on a location on said test device upstream from said test zone.

2. The test device of embodiment 1, wherein the first component and the second component are the same.

3. The test device of embodiment 1, wherein the first component and the second component are different.

4. The test device of embodiment 3, wherein one of the first component and the second component is a polynucleotide and the other is a non-polynucleotide moiety.

5. The test device of embodiment 4, wherein the first component is a polynucleotide and the second component is a non-polynucleotide moiety.

6. The test device of any of the embodiments 1-5, wherein the non-polynucleotide moiety is a polypeptide.

7. The test device of any of the embodiments 1-6, wherein the first component links the DNA dendrimer to a binding reagent that binds to an analyte.

8. The test device of any of the embodiments 1-6, wherein the first component links the DNA dendrimer to a binding reagent that binds to another binding reagent that binds to an analyte.

9. The test device of any of the embodiments 1-8, wherein the second component links the DNA dendrimer to a detectable label.

10. The test device of any of the embodiments 1-8, wherein the second component links the DNA dendrimer to another binding reagent that is linked to a detectable label.

11. The test device of any of the embodiments 1-10, which is to be used in a sandwich assay for the analyte and wherein the test reagent at the test zone binds to the analyte, a second binding reagent that binds to the analyte is used, the second binding reagent comprises a polynucleotide that is substantially complementary to a polynucleotide that is the first component of a DNA dendrimer.

12. The test device of any of the embodiments 1-10, which is to be used in a sandwich assay for the analyte and wherein the test reagent at the test zone binds to the analyte, a second binding reagent that binds to another binding reagent that binds to an analyte is used, the second binding reagent comprises a polynucleotide that is substantially complementary to a polynucleotide that is the first component of a DNA dendrimer.

13. The test device of any of the embodiments 1-10, which is to be used in a competitive assay for the analyte and wherein the test reagent at the test zone is an analyte or an analyte analog, a second binding reagent that binds to the analyte is used, the second binding reagent comprises a polynucleotide that is substantially complementary to a polynucleotide that is the first component of a DNA dendrimer, and the analyte or an analyte analog at the test zone competes with an analyte in the sample for binding to the second binding reagent.

14. The test device of any of the embodiments 1-10, which is to be used in a competitive assay for the analyte and wherein the test reagent at the test zone is an analyte or an analyte analog, a second binding reagent that binds to another binding reagent that binds to an analyte is used, the second binding reagent comprises a polynucleotide that is substantially complementary to a polynucleotide that is the first component of a DNA dendrimer, and the analyte or an analyte analog at the test zone competes with an analyte in the sample for binding to the binding reagent that is bound to the second binding reagent.

15. The test device of any of the embodiments 1-14, wherein the analyte, analyte analog, test reagent and/or binding reagent is an inorganic molecule, an organic molecule or a complex thereof.

16. The test device of embodiment 15, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

17. The test device of any of the embodiments 1-14, wherein the analyte is a polypeptide or a small molecule, and the test reagent and/or binding reagent that binds to the analyte is an antibody that binds to the polypeptide or small molecule.

18. The test device of any of the embodiments 1-14, wherein the analyte is a polynucleotide, and the test reagent and/or binding reagent that binds to the analyte is another polynucleotide that is substantially complementary to the analyte polynucleotide.

19. The test device of any of the embodiments 1-18, wherein the matrix comprises nitrocellulose, glass fiber, polypropylene, polyethylene (preferably of very high molecular weight), polyvinylidene flouride, ethylene vinylacetate, acrylonitrile and/or polytetrafluoro-ethylene.

20. The test device of any of the embodiments 1-19, wherein the matrix is in the form a strip or a circle.

21. The test device of any of the embodiments 1-20, wherein the matrix is a single element or comprises multiple elements.

22. The test device of any of the embodiments 1-21, which further comprises a sample application element upstream from and in fluid communication with the matrix.

23. The test device of any of the embodiments 1-22, which further comprises a liquid absorption element downstream from and in fluid communication with the matrix.

24. The test device of any of the embodiments 1-23, which further comprises a control zone comprising means for indicating proper flow of the liquid sample and/or a valid test result.

25. The test device of any of the embodiments 1-24, wherein at least a portion of the matrix is supported by a solid backing.

26. The test device of any of the embodiments 1-25, wherein a substance is dried on a portion of the matrix upstream from the test zone, the dried substance being capable of being moved by a liquid sample and/or a further liquid to the test zone and/or a control zone to generate a detectable signal, the dried substance being at least one of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer.

27. The test device of embodiment 26, wherein two substances are dried on a portion of the matrix upstream from the test zone, the dried substances being capable of being moved by a liquid sample and/or a further liquid to the test zone and/or a control zone to generate a detectable signal, the dried substances being at least two of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the label linkable to the DNA dendrimer;

are dried on a portion of the matrix upstream from the test zone, the dried substances, whether separately or in complex, being capable of being moved by a liquid sample and/or a further liquid to the test zone and/or a control zone to generate a detectable signal.

28. The test device of embodiment 26, wherein three substances are dried on a portion of the matrix upstream from the test zone, the dried substances being capable of being moved by a liquid sample and/or a further liquid to the test zone and/or a control zone to generate a detectable signal, the dried substances being all of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the label linkable to the DNA dendrimer.

29. The test device of any of the embodiments 26-28, wherein the substance(s) is dried on a conjugate element that is upstream from the test zone.

30. The test device of any of the embodiments 26-29, wherein the substance(s) is located downstream from a sample application place on the test device.

31. The test device of any of the embodiments 26-30, wherein the substance(s) is located upstream from a sample application place on the test device.

32. The test device of any of the embodiments 1-31, wherein the detectable label is a soluble label.

33. The test device of embodiments 32, wherein the soluble label is a soluble enzyme or fluorescent label.

34. The test device of any of the embodiments 1-31, wherein the detectable label is a particle label.

35. The test device of embodiments 34, wherein the particle label is a visible or a non-visible particle label.

36. The test device of embodiments 35, wherein the visible particle label is selected from the group consisting of a gold particle, a latex particle, a Q-Dot, a carbon nanotube, a silver particle, a silver coated particle and a complex thereof.

37. The test device of embodiments 35, wherein the non-visible particle label is a fluorescent particle.

38. The test device of any of the embodiments 26-37, wherein the substance(s) is dried in the presence of a material that: a) stabilizes the dried substance(s); b) facilitates solubilization or resuspension of the dried substance(s) in a liquid; and/or c) facilitates mobility of the dried substance(s).

39. The test device of embodiments 38, wherein the material is selected from the group consisting of a protein, a peptide, a polysaccharide, a sugar, a polymer, a gelatin and a detergent.

40. The test device of any of the embodiments 1-39, wherein a sample liquid alone is used to transport the analyte and/or the substance(s) to the test zone.

41. The test device of any of the embodiments 1-39, wherein a developing liquid is used to transport the analyte and/or the substance(s) to the test zone.

42. The test device of any of the embodiments 1-41, which further comprises a housing that covers at least a portion of the test device, wherein the housing comprises a sample application port to allow sample application upstream from or to the test zone and an optic opening around the test zone to allow signal detection at the test zone.

43. The test device of embodiment 42, wherein the housing covers the entire test device.

44. The test device of embodiment 42, wherein at least a portion of the sample receiving portion of the matrix or the sample application element is not covered by the housing and a sample is applied to the portion of the sample receiving portion of the matrix or the sample application element outside the housing and then transported to the test zone.

45. The test device of any of the embodiments 1-44, wherein none of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer;

is covalently crosslinked to each other.

46. The test device of any of the embodiments 1-44, wherein at least two of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer;

are covalently crosslinked to each other.

47. The test device of any of the embodiments 1-44, wherein all of:

1) the DNA dendrimer;

2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and 3) the detectable label linkable to the DNA dendrimer; are covalently crosslinked to each other.

48. The test device of any of the embodiments 1-47, wherein the DNA dendrimer comprises from about 10 to about 1,500, preferably from about 40 to about 1,500, from about 900 to about 1,100, second components that link the DNA dendrimer to a detectable label linkable to the DNA dendrimer.

49. The test device of any of the embodiments 1-48, wherein the DNA dendrimer comprises from about 400 to about 80,000, preferably from about 4,000 to about 80,000, from about 60,000 to about 80,000, DNA nucleotides.

50. The test device of any of the embodiments 1-49, wherein the DNA dendrimer comprises a one-layer, a two-layer, a three-layer or a four-layer structure.

51. The test device of any of the embodiments 1-50, wherein the liquid sample has moved laterally along the test device to generate a detectable signal at the test zone.

52. A method for detecting an analyte in a liquid sample, which method comprises:
    a) contacting a liquid sample with the test device of any of the embodiments 1-50, wherein the liquid sample is applied to a site of the test device upstream of the test zone;
    b) transporting an analyte, if present in the liquid sample, a detectable label and a DNA dendrimer to the test zone; and
    c) assessing the presence, absence, and/or amount of a signal generated by the detectable label at the test zone to determining the presence, absence and/or amount of the analyte in the liquid sample.

53. The method of embodiment 52, wherein the liquid sample and at least one of:
    1) the DNA dendrimer;
    2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and
    3) the detectable label linkable to the DNA dendrimer; are premixed to form a mixture and the mixture is applied to the test device.

54. The method of embodiment 52, wherein the liquid sample and at least two of:
    1) the DNA dendrimer;
    2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and
    3) the detectable label linkable to the DNA dendrimer; are premixed to form a mixture and the mixture is applied to the test device.

55. The method of embodiment 52, wherein the liquid sample and all of:
    1) the DNA dendrimer;
    2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and
    3) the detectable label linkable to the DNA dendrimer; are premixed to form a mixture and the mixture is applied to the test device.

56. The method of any of the embodiments 52-55, which is conducted in a liquid comprising from about 0.001% (v/v) to about 5% (v/v), preferably, from about 0.01% (v/v) to about 0.5% (v/v), or at about 0.01% (v/v) or less Tween-20.

57. The method of any of the embodiments 52-56, which is conducted in a liquid comprising dextran sulfate.

58. The method of embodiment 52, wherein a substance is dried on a portion of the test device upstream from the test zone, the dried substance is solubilized or resuspended, and transported to the test zone and/or a control zone to generate a detectable signal, the dried substance being at least one of:
    1) the DNA dendrimer;
    2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer; and
    3) the detectable label linkable to the DNA dendrimer.

59. The method of embodiment 58, wherein the dried substance is located downstream from the sample application site, and the dried substance is solubilized or resuspended, and transported to the test zone and/or a control zone by the liquid sample.

60. The method of embodiment 58, wherein the dried substance is located upstream from the sample application site, and the dried substance is solubilized or resuspended, and transported to the test zone and/or a control zone by another liquid.

61. The method of embodiment 58, wherein the dried substance is solubilized or resuspended, and transported to the test zone and/or a control zone by the liquid sample alone.

62. The method of embodiment 58, wherein the analyte and/or dried substance is solubilized or resuspended, and transported to the test zone and/or a control zone by another liquid.

63. The method of any of the embodiments 52-62, wherein the liquid sample is a body fluid sample.

64. The method of embodiment 63, wherein the body fluid sample is selected from the group consisting of a whole blood, a serum, a plasma and a urine sample.

65. The method of any of the embodiments 52-64, wherein the liquid sample is a sample derived from a biological, a forensics, a food, a biowarfare, or an environmental source.

66. The method of any of the embodiments 52-65, which is used to quantify or semi-quantify the amount of an analyte in a liquid sample.

67. The method of any of the embodiments 52-66, which is used to detect multiple analytes in a liquid sample.

68. The method of embodiment 67, which is used to quantify or semi-quantify the amounts of the multiple analytes in the liquid sample.

69. The method of any of the embodiments 52-68, wherein the analyte is selected from the group consisting of a cell, a virus and a molecule.

70. A test device for detecting an analyte in a liquid sample, which device comprises a porous matrix that comprises a test zone on said porous matrix, said test zone comprising a test reagent that binds to an analyte or another binding reagent that binds to said analyte, or is an analyte or an analyte analog that competes with an analyte in said sample for binding to a binding reagent for said analyte, wherein a liquid sample flows laterally along said test device and passes said test zone to form a detectable signal to indicate presence, absence and/or amount of said analyte in said liquid sample, the formation of said detectable signal requires the use of a DNA dendrimer linked to a detectable label non-covalently, and said DNA dendrimer comprises a component that links said DNA dendrimer to a binding reagent linkable to said DNA dendrimer, an analyte linkable to said DNA dendrimer, or an analyte analog linkable to said DNA dendrimer, and wherein:

a) said analyte is not a polynucleotide; or b) said DNA dendrimer comprises from about 1 to about 324, preferably from about 60 to about 324, from about 80 to about 300 or from about 100 to about 200, said first components; or c) said DNA dendrimer, before said test device is used, is dried on a location on said test device upstream from said test zone.

71. The test device of embodiment 70, wherein the component is a polynucleotide.

72. The test device of embodiment 70 or 71, which is to be used in a sandwich assay for the analyte and wherein the test reagent at the test zone binds to the analyte, a second binding reagent that binds to the analyte is used, the second binding reagent comprises a polynucleotide that is substantially complementary to a polynucleotide that is the component of a DNA dendrimer.

73. The test device of embodiment 70 or 71, which is to be used in a sandwich assay for the analyte and wherein the test reagent at the test zone binds to the analyte, a second binding reagent that binds to another binding reagent that binds to an analyte is used, the second binding reagent comprises a polynucleotide that is substantially complementary to a polynucleotide that is the component of a DNA dendrimer.

74. The test device of embodiment 70 or 71, which is to be used in a competitive assay for the analyte and wherein the test reagent at the test zone is an analyte or an analyte analog, a second binding reagent that binds to the analyte is used, the second binding reagent comprises a polynucleotide that is substantially complementary to a polynucleotide that is the component of a DNA dendrimer, and the analyte or an analyte analog at the test zone competes with an analyte in the sample for binding to the second binding reagent.

75. The test device of embodiment 70 or 71, which is to be used in a competitive assay for the analyte and wherein the test reagent at the test zone is an analyte or an analyte analog, a second binding reagent that binds to another binding reagent that binds to an analyte is used, the second binding reagent comprises a polynucleotide that is substantially complementary to a polynucleotide that is the component of a DNA dendrimer, and the analyte or an analyte analog at the test zone competes with an analyte in the sample for binding to the binding reagent that is bound to the second binding reagent.

76. The test device of any of the embodiments 70-75, wherein the analyte, analyte analog, test reagent and/or binding reagent is an inorganic molecule, an organic molecule or a complex thereof.

77. The test device of embodiment 76, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

78. The test device of any of the embodiments 70-77, wherein the analyte is a polypeptide or a small molecule, and the test reagent and/or binding reagent that binds to the analyte is an antibody that binds to the polypeptide or small molecule.

79. The test device of any of the embodiments 70-77, wherein the analyte is a polynucleotide, and the test reagent and/or binding reagent that binds to the analyte is another polynucleotide that is substantially complementary to the analyte polynucleotide.

80. The test device of any of the embodiments 70-79, wherein the matrix comprises nitrocellulose, glass fiber, polypropylene, polyethylene (preferably of very high molecular weight), polyvinylidene flouride, ethylene vinylacetate, acrylonitrile and/or polytetrafluoro-ethylene.

81. The test device of any of the embodiments 70-80, wherein the matrix is in the form a strip or a circle.

82. The test device of any of the embodiments 70-81, wherein the matrix is a single element or comprises multiple elements.

83. The test device of any of the embodiments 70-82, which further comprises a sample application element upstream from and in fluid communication with the matrix.

84. The test device of any of the embodiments 70-83, which further comprises a liquid absorption element downstream from and in fluid communication with the matrix.

85. The test device of any of the embodiments 70-84, which further comprises a control zone comprising means for indicating proper flow of the liquid sample and/or a valid test result.

86. The test device of any of the embodiments 70-85, wherein at least a portion of the matrix is supported by a solid backing.

87. The test device of any of the embodiments 70-86, wherein a substance is dried on a portion of the matrix upstream from the test zone, the dried substance being capable of being moved by a liquid sample and/or a further liquid to the test zone and/or a control zone to generate a detectable signal, the dried substance being at least one of:

1) the DNA dendrimer; and 2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer.

88. The test device of embodiments 87, wherein both of the DNA dendrimer, and the first binding reagent that binds to the analyte, the second binding reagent that binds to another binding reagent that binds to the analyte, the analyte or the analyte analog, are dried on a portion of the matrix upstream from the test zone.

89. The test device of embodiment 87 or 88, wherein the substance(s) is dried on a conjugate element that is upstream from the test zone.

90. The test device of embodiment 87 or 88, wherein the substance(s) is located downstream from a sample application place on the test device.

91. The test device of embodiment 87 or 88, wherein the substance(s) is located upstream from a sample application place on the test device.

92. The test device of any of the embodiments 70-91, wherein the detectable label is a soluble label.

93. The test device of embodiments 92, wherein the soluble label is a soluble enzyme or fluorescent label.

94. The test device of any of the embodiments 70-91, wherein the detectable label is a particle label.

95. The test device of embodiments 94, wherein the particle label is a visible or a non-visible particle label.

96. The test device of embodiments 95, wherein the visible particle label is selected from the group consisting of a gold particle, a latex particle, a Q-Dot, a carbon nanotube, a silver particle, a silver coated particle and a complex thereof.

97. The test device of embodiments 95, wherein the non-visible particle label is a fluorescent particle.

98. The test device of any of the embodiments 87-97, wherein the substance(s) is dried in the presence of a material that: a) stabilizes the dried substance(s); b) facilitates solubilization or resuspension of the dried substance(s) in a liquid; and/or c) facilitates mobility of the dried substance(s).

99. The test device of embodiments 98, wherein the material is selected from the group consisting of a protein, a peptide, a polysaccharide, a sugar, a polymer, a gelatin and a detergent.

100. The test device of any of the embodiments 70-99, wherein a sample liquid alone is used to transport the analyte and/or the substance(s) to the test zone.

101. The test device of any of the embodiments 70-99, wherein a developing liquid is used to transport the analyte and/or the substance(s) to the test zone.

102. The test device of any of the embodiments 70-101, which further comprises a housing that covers at least a portion of the test device, wherein the housing comprises a sample application port to allow sample application upstream from or to the test zone and an optic opening around the test zone to allow signal detection at the test zone.

103. The test device of embodiment 102, wherein the housing covers the entire test device.

104. The test device of embodiment 102, wherein at least a portion of the sample receiving portion of the matrix or the sample application element is not covered by the housing and a sample is applied to the portion of the sample receiving portion of the matrix or the sample application element outside the housing and then transported to the test zone.

105. The test device of any of the embodiments 70-104, wherein the DNA dendrimer comprises from about 1 to about 324, preferably from about 60 to about 324, from about 80 to about 300 or from about 100 to about 200, said first components.

106. The test device of any of the embodiments 70-105, wherein the DNA dendrimer comprises from about 10 to about 1,500, preferably from about 40 to about 1,500 or from about 900 to about 1,100, the detectable label.

107. The test device of any of the embodiments 70-106, wherein the DNA dendrimer comprises from about 400 to about 80,000, preferably from about 4,000 to about 80,000, or from about 60,000 to about 80,000, DNA nucleotides.

108. The test device of any of the embodiments 70-107, wherein the DNA dendrimer comprises a one-layer, a two-layer, a three-layer or a four-layer structure.

109. The test device of any of the embodiments 70-108, wherein the liquid sample has moved laterally along the test device to generate a detectable signal at the test zone.

110. A method for detecting an analyte in a liquid sample, which method comprises:
a) contacting a liquid sample with the test device of any of the embodiments 70-108, wherein the liquid sample is applied to a site of the test device upstream of the test zone;
b) transporting an analyte, if present in the liquid sample, a detectable label and a DNA dendrimer to the test zone; and
c) assessing the presence, absence, and/or amount of a signal generated by the detectable label at the test zone to determining the presence, absence and/or amount of the analyte in the liquid sample.

111. The method of embodiment 110, wherein the liquid sample and at least one of:
1) the DNA dendrimer linked to a detectable label non-covalently; and
2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer;
are premixed to form a mixture and the mixture is applied to the test device.

112. The method of embodiment 110, wherein the liquid sample and both of:
1) the DNA dendrimer linked to a detectable label non-covalently; and
2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer;
are premixed to form a mixture and the mixture is applied to the test device.

113. The method of any of the embodiments 110-112, which is conducted in a liquid comprising from about 0.001% (v/v) to about 5% (v/v), preferably, from about 0.01% (v/v) to about 0.5% (v/v), or at about 0.01% (v/v) or less Tween-20.

114. The method of any of the embodiments 110-113, which is conducted in a liquid comprising dextran sulfate.

115. The method of embodiment 110, wherein a substance is dried on a portion of the test device upstream from the test zone, the dried substance is capable of being moved by a liquid sample and/or a further liquid to the test zone and/or a control zone to generate a detectable signal, the dried substance being at least one of:
1) the DNA dendrimer linked to a detectable label non-covalently; and
2) the first binding reagent that binds to the analyte, the second binding reagent that binds to another binding reagent that binds to the analyte, the analyte or the analyte analog, each of the first binding reagent, second binding reagent, analyte or analyte analog being linkable to the DNA dendrimer.

116. The method of embodiment 115, wherein the dried substance is located downstream from the sample application site, and the dried substance is solubilized or resuspended, and transported to the test zone and/or a control zone by the liquid sample.

117. The method of embodiment 115, wherein the dried substance is located upstream from the sample application site, and the dried substance is solubilized or resuspended, and transported to the test zone and/or a control zone by another liquid.

118. The method of embodiment 115, wherein the dried substance is solubilized or resuspended, and transported to the test zone and/or a control zone by the liquid sample alone.

119. The method of embodiment 115, wherein the analyte and/or dried substance is solubilized or resuspended, and transported to the test zone and/or a control zone by another liquid.

120. The method of any of the embodiments 110-119, wherein the liquid sample is a body fluid sample.

121. The method of embodiment 120, wherein the body fluid sample is selected from the group consisting of a whole blood, a serum, a plasma and a urine sample.

122. The method of any of the embodiments 110-121, wherein the liquid sample is a sample derived from a biological, a forensics, a food, a biowarfare, or an environmental source.

123. The method of any of the embodiments 110-122, which is used to quantify or semi-quantify the amount of an analyte in a liquid sample.

124. The method of any of the embodiments 110-123, which is used to detect multiple analytes in a liquid sample.

125. The method of embodiment 124, which is used to quantify or semi-quantify the amounts of the multiple analytes in the liquid sample.

126. The method of any of the embodiments 110-125, wherein the analyte is selected from the group consisting of a cell, a virus and a molecule.

G. Examples

The following examples represent applications of the above descriptions of using DNA dendrimers in POC lateral flow assays. The following examples are included for illustrative purposes only and are not intended to limit the scope of the invention.

EXAMPLE 1

Figure 3:
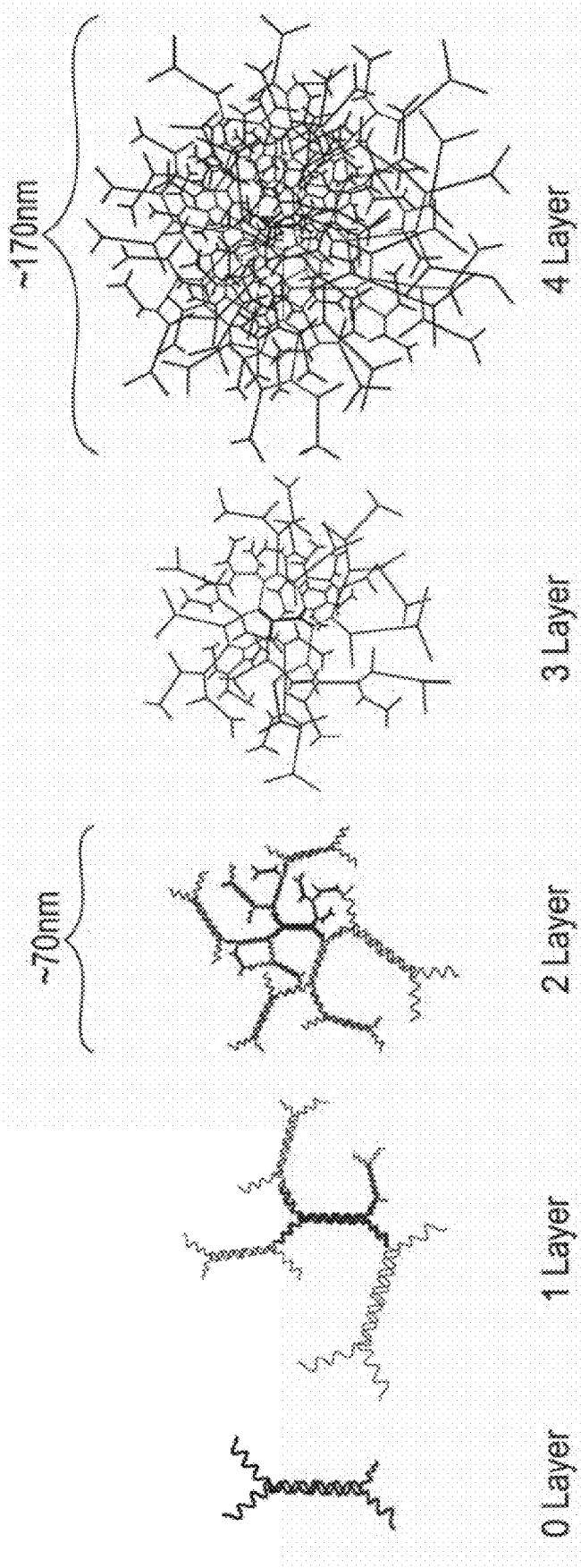
FIG. 3 illustrates an exemplary manufacturing DNA dendrimers: Stepwise "assembly" of the dendrimer structure. Dendrimers are assembled from 5partially double stranded "monomers" added in a controlled step-by-step process. In some embodiments, the final dendrimer matrix structure is fully covalent via the addition of a psorlen crosslinking intercalation reagent during the assembly process.

Use of a DNA Dendrimer and an Anti-hCG Mouse Monoclonal Targeting Antibody-Oligo Conjugate to Improve Sensitivity in an all Liquid ("Wet"), Direct Sandwich POC Lateral Flow Assay Manufacture of the DNA Dendrimer DNA dendrimers are manufactured as previously disclosed (see U.S. Pat. Nos. 5,175,270, 5,484,904, 5,487,973, 6,110,687, and 6,274,723). Briefly, a DNA dendrimer is constructed from DNA monomers, each of which is made from two DNA strands that share a region of sequence complementarity located in the central portion of each strand. When the two strands anneal to form the monomer the resulting structure can be described as having a central double-stranded "waist" bordered by four single-stranded "arms". This waist-plus-arms structure comprises the basic DNA monomer. The single-stranded arms at the ends of each of the five monomer types are designed to interact with one another in precise and specific ways. Base-pairing between the arms of complementary monomers allows directed assembly of the dendrimer through sequential addition of monomer layers (FIG. 3). Assembly of each layer of the dendrimer includes a cross-linking process where the strands of DNA are covalently bonded to each other, thereby forming a completely covalent molecule impervious to denaturing conditions that otherwise would cause deformation of the dendrimer structure (FIG. 2). In addition, 38 base oligonucleotides that serve as complementary capture oligos are pre-ligated to the 5' ends of an separate 124mer single-stranded DNA oligonucleotide via a simple T4 DNA ligase-dependent ligation reaction ("strand ligate"), as follows:

| 124mer DNA strand | 500 ng |
| e(+)LIG-BR7 Bridging oligo (14mer) | 241.9 ng |
| ligA Cap03 oligo (38mer) | 306.5 ng |
| 10× Ligase buffer | 1 uL (1/10 volume) |
| Nuclease free water | to 10 uL total volume |
| T4 DNA Ligase (1 U/uL) | 1 uL (1 unit, 1/10 volume) |

The first five reactants are added together, incubated at 42° C. for 15 minutes and then allowed to cool to room temperature. The 6$^{th}$ reactant is then added and incubated for 2 hours. The ligation reaction is stopped by adding 0.25 uL of 0.5M EDTA solution (to 12.5 mM final). This strand ligate is used in the manufacture of the capture sequence specific biotinylated DNA dendrimer below.

The strand ligate (above) and DNA oligonucleotides containing biotin label moieties are covalently bound to the peripheral single stranded DNA sequences of the dendrimer via hybridization followed by intercalation of psoralen between the two hybridized strands of DNA. The intercalated psoralen becomes covalently bound between the hybridized DNA strands when exposed to 300 nm UV light.

A typical manufacturing hybridization-crosslinking process would be:

Add to a microfuge tube the following components:

| 4 layer DNA dendrimer | 1000 ng (1 ug) |
| strand ligate (from above) | 500 ng as strand (total synthesis 10uL) |
| c(+) 2x biotin oligo (35mer) (complementary to dendrimer "c arm") | 452.4 ng |
| N3(−) #1 2x biotin oligo (18mer) (complementary to "strand 3 ligate") | 291.9 ng |
| N3(−) #2 2x biotin oligo (19mer) (complementary to "strand 3 ligate") | 243.2 ng |
| N3(−) #3 2x biotin oligo (26mer) (complementary to "strand 3 ligate") | 316.2 ng |
| 5M NaCl | 1.1 uL (0.2M Final) |
| 0.1M DTT | 0.7 uL (2.5 mM Final) |
| Nuclease free Water | to 28 uL total volume |
| 2,4,8 trimethyl psoralen saturated solution in ethanol | 1.1 uL |

The above reactants are added together, mixed well, placed into a container of water at 75° C. and slow cooled to 42° C. Exposure to 300 nm UV light for 10 minutes initiates a cross-linking event covalently binding the biotinylated oligos to the arms of the DNA dendrimer. An additional 1.1 uL of psoralen saturated solution in ethanol is added and the reactants are exposed to an additional 2.5 minute exposure to 300 nm UV light. Non-cross-linked oligonucleotides are removed via the use of a size exclusion spin column or equivalent method.

For dendrimers containing more or less capture sequences, the quantity of "strand ligate" (reactant 2 above) can be varied accordingly.

Figure 4:
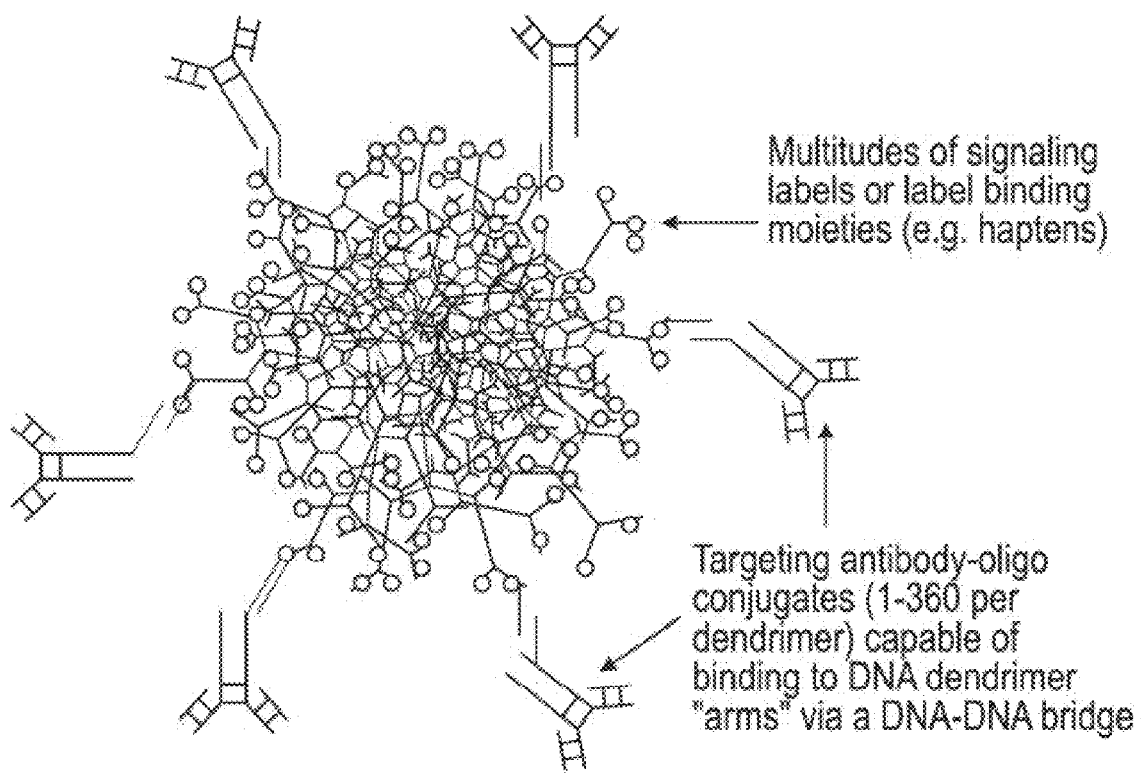
FIG. 4 illustrates an exemplary dendrimer molecule containing targeting antibodies and labels for immunoassays.

A mouse anti-hCG targeting antibody (DCN, Carlsbad, Calif.) was conjugated to the cplCap03 DNA oligonucleotide, which is complementary to the Cap03 DNA oligonucleotide previously ligated to the dendrimer-bound "strand ligate". The cplCap03 DNA oligonucleotide is covalently conjugated to the anti-mouse IgG antibody using standard cross-linking condensation conjugation chemistry. This antibody-oligo conjugate may be used as a separate reagent in the lateral flow assay, or may be pre-combined with the DNA dendrimer via the hybridization of the antibody-bound cplCap03 oligonucleotide to the complementary Cap03 sequence on the peripheral "arms" of the dendrimer. This hybridization site comprises 31 base pairs and has a melting temperature of greater than 65° C., thereby providing a stable complex of dendrimer bound with antibody at physiological temperatures and conditions (FIG. 4).

Performance of the POC Lateral Flow Assay Utilizing DNA Dendrimers as Signal Amplifiers:

The following materials were required:
1. Lateral flow strips consisting of a) nitrocellulose membranes (HF180, EMD Millipore, Billerica, Mass.) and b) wick material. The nitrocellulose membranes were striped with an anti-hCG alpha antibody at a concentration suitable for lateral flow immunoassay applications for use as a test line as well as an additional stripe of an anti-mouse IgG antibody for use as a control line. All components were appropriately blocked and prepared for standard lateral flow immunoassays.
2. Liquid (aqueous) samples containing known amounts of hCG.
3. Mouse anti-hCG (beta) antibody-oligo conjugate for use as a targeting molecule for dendrimer binding, in solution.
4. DNA dendrimer, biotinylated and containing the Cap03 capture sequence (as described above), in an aqueous buffer solution.
5. Streptavidin-conjugated colloidal gold nanoparticles (40 nm nominal size), in solution (Diagnostics Consulting Network (DCN), Carlsbad, Calif.).
6. Phosphate buffered saline (PBS) with 0.05% Tween-20 (T) and 0.5% BSA (B) (PBS-TB).
7. Mouse anti-hCG colloidal gold conjugate (40 nm nominal size), in solution (DCN).
8. 96 well polystyrene microtiter plates with flat bottom wells.

Assay procedure (multi-step):
1. All reagents were diluted using PBS-TB.
2. Into the first row of a 96 well microtiter plate, 15µl of the appropriate amount of hCG antigen (range starting at 100 mIU with two-fold serial dilutions down to 0.024 mIU) were dispensed.
3. Into the second row, 15µl of the mouse anti-hCG antibody-oligonucleotide conjugate at the correct dilution (1:100, determined empirically) were dispensed.
4. Into the third row, 15µl of dendrimer diluted to 13.3 ng/µl (for a total final working amount of dendrimer per well/per lateral flow strip to be 200 ng) were dispensed.
5. Into the fourth row, 20µl of streptavidin-colloidal gold conjugate diluted to 1.0 OD were dispensed.
6. The strips were placed into the wells of row 1 (containing the hCG antigen) and the strips were leaned towards the rear of the plate so that the bottom of the strip remained in contact with the solution at the front of the well.
7. Once all the liquid in the wells of the first row had been wicked into all of the strips, the strips were moved to the next row of wells. This process was repeated for each strip into succeeding wells until all liquid in each well has been absorbed by the corresponding strip.
8. After all strips had been moved successfully through all the wells, the visual score of the each test line was recorded (as per a standard lateral flow visual scoring guide as per DCN). A visible reddish or brown-reddish line at both the test and control lines indicated a valid positive result (the successful detection of hCG in the sample). A visible control line only indicated a valid negative result (no detection of hCG in the sample). The lack of any visible control line indicated an invalid test and the results were discarded.
9. To set up a standard assay, follow the above procedure and replace both the mouse anti-hCG antibody-oligo conjugate and 3DNA® dendrimer (a proprietary dendritic molecule comprised solely of DNA) with 15µl of PBS-T and replace the streptavidin colloidal gold conjugate with a mouse anti-hCG colloidal gold conjugate (diluted to a working concentration of 1.0 OD).

Figure 5A:
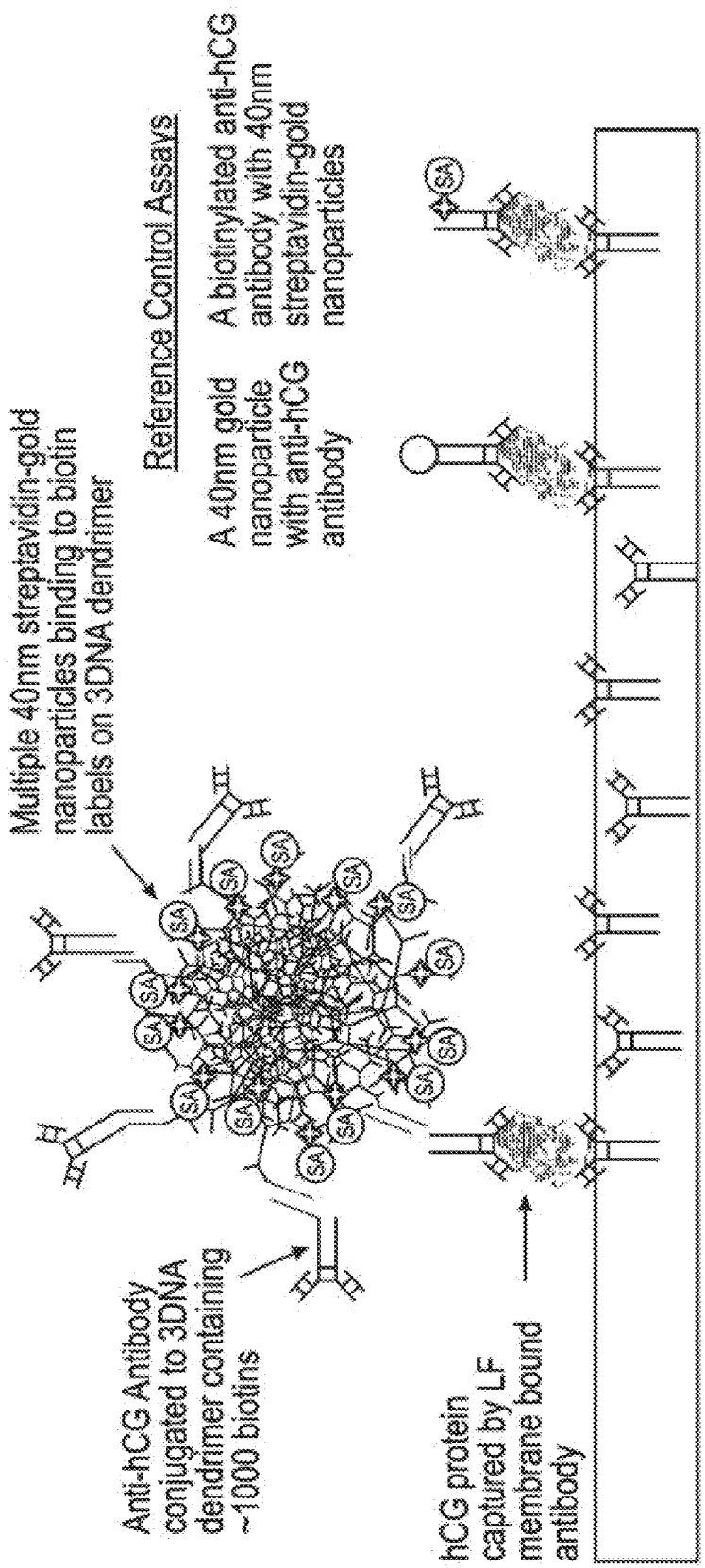
FIG. 5A illustrates protein detection by 3DNA® Dendrimers (a proprietary dendritic molecule comprised solely of DNA) in a model hCG lateral flow POC assay (direct sandwich method).
Figure 5B:
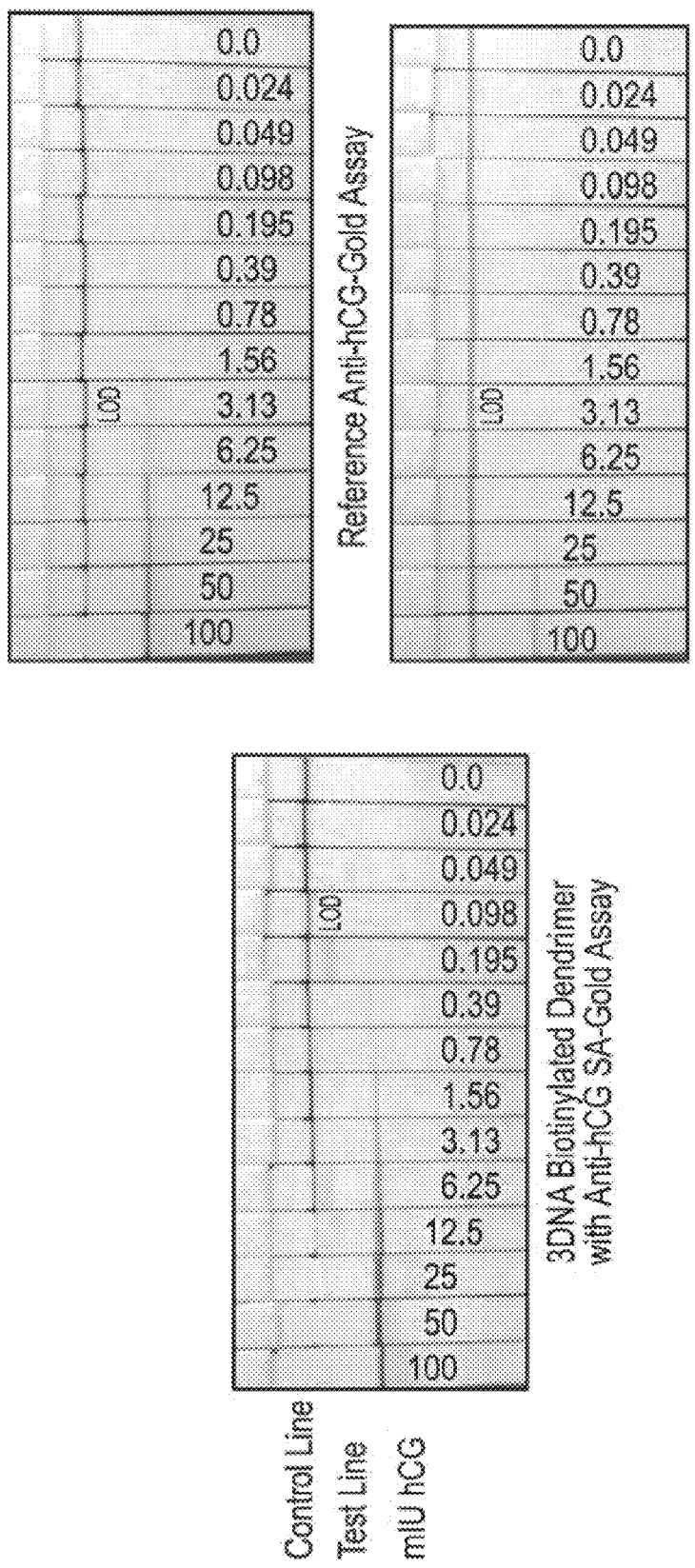
FIG. 5B illustrates DNA dendrimer, anti-hCG antibody-oligo conjugate and gold reagents were added as liquid components during the performance of an exemplary dendrimer lateral flow assay. In some embodiments, 3DNA® Dendrimer (a proprietary dendritic molecule comprised solely of DNA) assay is 16 fold more sensitive than anti-hCG gold standard assay, and ~32 fold more sensitive than biotinylated anti-hCG SA-gold standard assay.
Figure 5C:
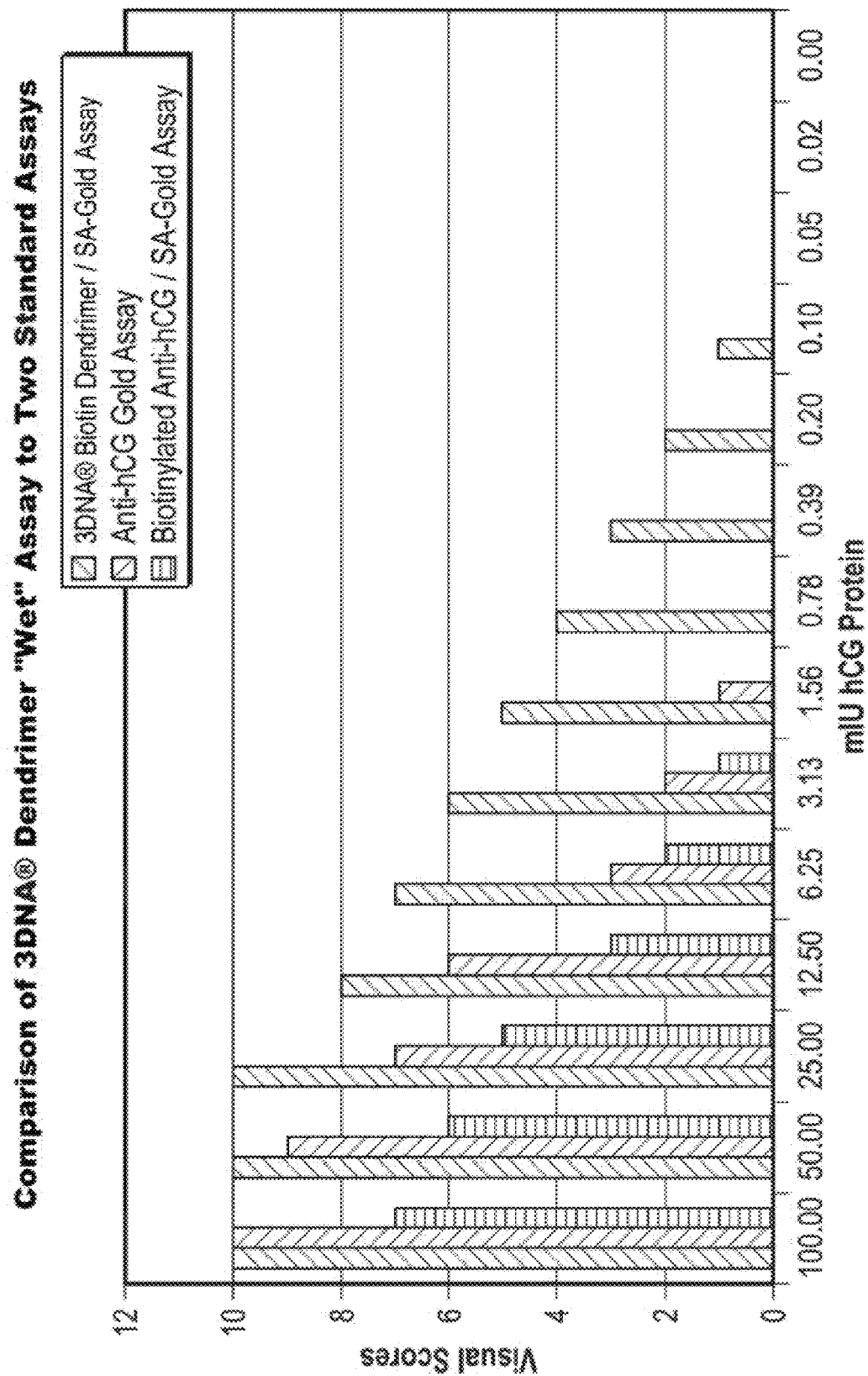
FIG. 5C illustrates comparison of 3DNA® Dendrimer (a proprietary dendritic molecule comprised solely of DNA) "wet" assay to two standard assays.

Results of utilizing a 3DNA® dendrimer (a proprietary dendritic molecule comprised solely of DNA) in a direct sandwich POC lateral flow hCG assay (wet assay format):

After performing the above described assay on hCG samples that range from 100 mIU down to 0.024 mIU in two-fold serial dilutions, it was observed that a limit of detection (LOD) of 0.20-0.40 mIU hCG was achieved for the dendrimer assay, compared to a LOD of 3.1-6.2 mIU for the non-dendrimer standard hCG assay, resulting in a 8-32 fold improvement of sensitivity when using the DNA dendrimer as a signal amplifier (FIG. 5).

EXAMPLE 2

Use of a 3DNA Dendrimer and an Anti-Mouse IgG Targeting Antibody-Oligo Conjugate to Improve Sensitivity in an all Liquid ("Wet"), Indirect Sandwich POC Lateral Flow Assay The following materials were required:
1. Lateral flow strips as described in Example 1.
2. Liquid (aqueous) samples containing hCG antigen as described in Example 1.
3. Mouse anti-hCG (beta) antibody to be used as a primary antibody (1:1000 dilution, determined empirically) (DCN).
4. Anti-mouse antibody-oligo conjugate for use as a targeting molecule for dendrimer binding, in solution.
5. 3DNA biotinylated dendrimer, in solution.
6. Streptavidin-conjugated colloidal gold nanoparticles, as described in Example 1.
7. PBS-TB, as described in Example 1.
8. Mouse anti-hCG colloidal gold conjugate, as described in Example 1.
9. 96 well polystyrene microtiter plates as described in Example 1.

Assay procedure (multi-step): The assay was performed as in Example 1, except for the following steps:
3. Into the second row, dispense 15 µl of the mouse anti-hCG antibody at the correct dilution (1:1000, determined empirically).
4. Into the third row, dispense 15 µl of the anti-mouse antibody-oligo conjugate at the correct dilution (1:18, determined empirically).
5. Into the fourth row, dispense 15 µl of dendrimer diluted to 13.3 ng/µl (for a total final working amount of dendrimer per well/per lateral flow strip to be 200 ng).
6. Into the fifth row, dispense 20 µl of streptavidin-colloidal gold conjugate diluted to 1.0 OD.
7. The remaining steps were performed in a manner identical to steps 7-9 of Example 1.

Figure 6A:
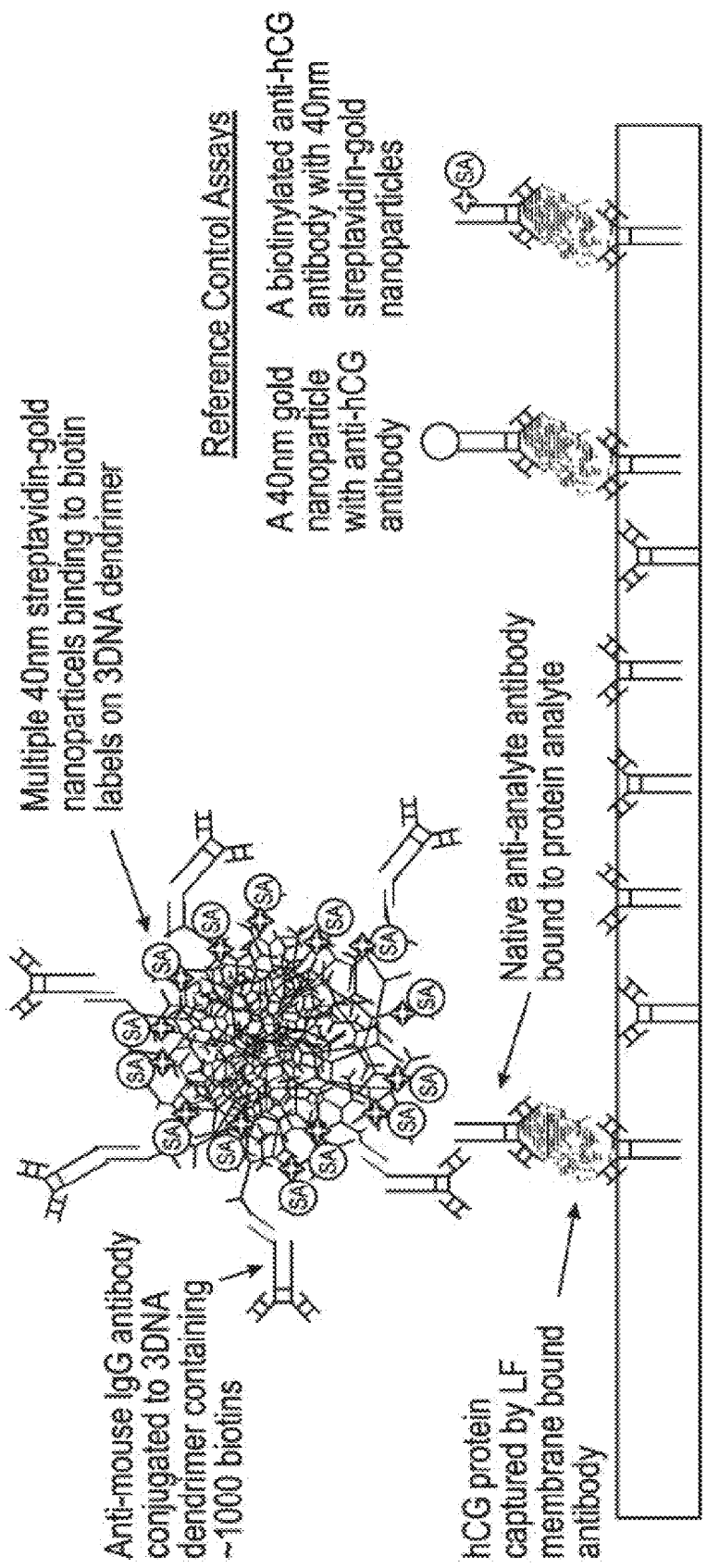
FIG. 6A illustrates protein detection by 3DNA® Dendrimers (a proprietary dendritic molecule comprised solely of DNA) in a model hCG lateral flow POC assay (indirect sandwich method).
Figure 6B:
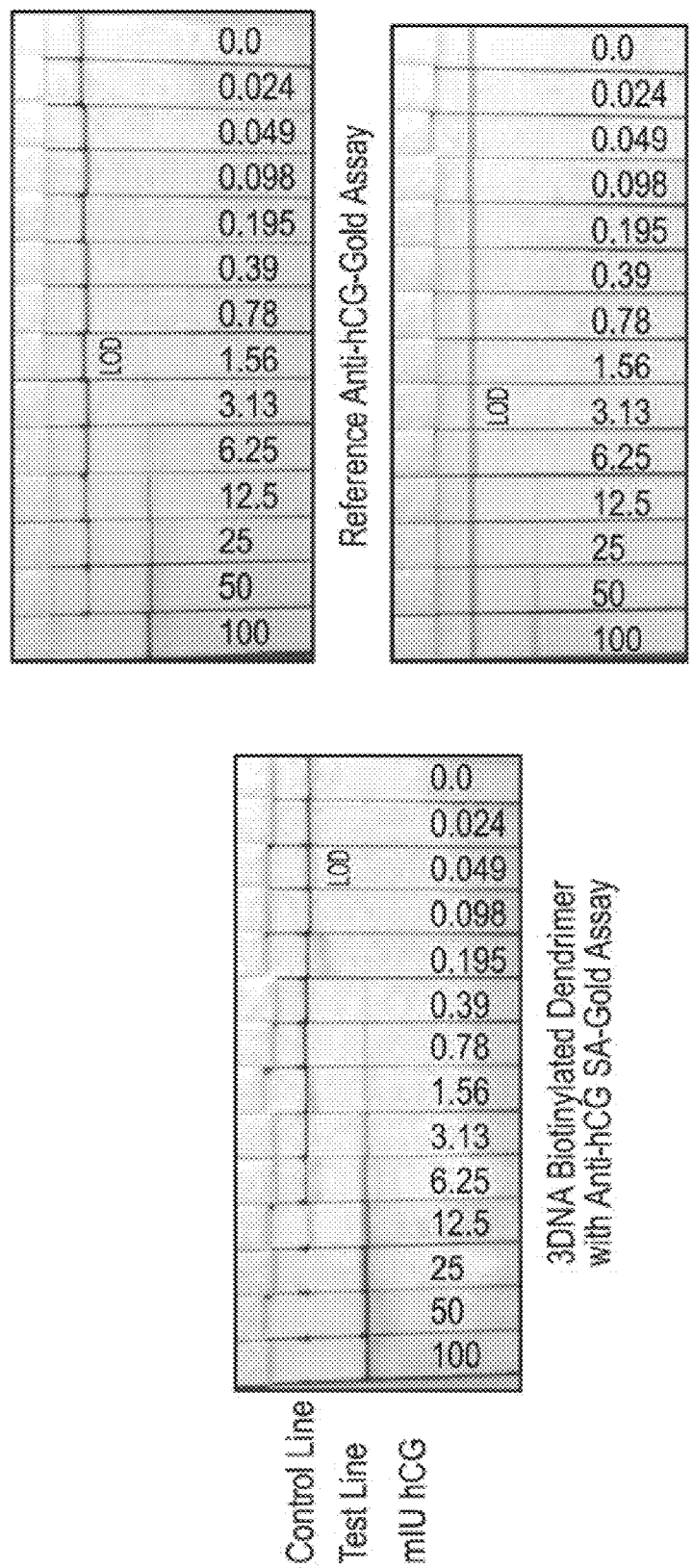
FIG. 6B illustrates DNA dendrimer, anti-hCG antibody-oligo conjugate, native antibody and gold reagents were added as liquid components during the performance of an exemplary dendrimer lateral flow assay. In some embodiments, 3DNA® Dendrimer (a proprietary dendritic molecule comprised solely of DNA) Assay is 16 fold more sensitive than anti-hCG Gold Standard assay, and ~32 fold more sensitive than biotinylated anti-hCG SA-Gold Standard assay.

Results of Utilizing a DNA Dendrimer in an Indirect Sandwich POC Lateral Flow hCG Assay (Wet Assay Format):

After performing the above described assay on hCG samples that range from 100 mIU down to 0.024 mIU in two-fold serial dilutions, it was observed that a limit of detection (LOD) of 0.10-0.20 mIU hCG was achieved for the dendrimer assay, compared to a LOD of 3.1-6.2 mIU for the non-dendrimer standard hCG assay, resulting in a 16-64 fold improvement of sensitivity when using the DNA dendrimer as a signal amplifier (FIG. 6).

EXAMPLE 3

Effect of Various Physical Characteristics of DNA Dendrimers on Performance in Direct Sandwich POC Lateral Flow Assays as Performed in Example 1

Materials required: as in Example 1, except different DNA dendrimers were utilized as described below.

Assay procedure (multi-step): the assay was performed as in Example 1 except that different DNA dendrimers were used as described below.

Effect of Number of Capture Sequences

The antibody-oligo conjugate, capable of binding either directly or indirectly to analyte in a POC assay, "bridges" or binds to a DNA oligonucleotide "capture" sequence previously incorporated into a DNA dendrimer signal amplifier. The number of oligonucleotide "capture" sequences manufactured into the DNA dendrimer (via hybridization and crosslinking of said arm) can be varied. DNA dendrimers containing ~60, ~120 or ~160 "capture" sequences were synthesized as described previously. These DNA dendrimers were then utilized in a direct sandwich POC lateral flow assay ("wet" format) as described in Example #1.

It was observed that as the number of capture sequences are increased, a lower LOD was achieved in the hCG detection assay. As sensitivity increased to the highest levels, non-specific binding (NSB) was observed in the assay, which was partially controlled via the use of various reaction buffers, detergents and other reagents. These results supported that a higher number of antibody-oligo conjugate binding sites on the DNA dendrimers improved the sensitivity of the assay, likely via improvement of reaction kinetics via the increased likelihood of contact between the analyte, the antibody-oligo conjugate and the DNA dendrimer signal amplifier.

Effect of Number of Labels

The total number of label moieties (e.g., biotin) was varied on the DNA dendrimers. DNA dendrimers were synthesized with ~1,440, ~960, ~480, and ~240 biotins. It was observed that DNA dendrimers containing ~960 biotins performed best, followed by ~1,440, ~480 and ~240 biotins respectively. The poorer sensitivity of the DNA dendrimer with ~1,440 biotins was unexpected and may have been due to the somewhat larger size of this molecular reagent as compared to the other dendrimers, which may have kinetically disfavored the maximally labeled dendrimer in the immunoassay.

Effect of Size

DNA dendrimers can be synthesized to be of various physical sizes, which may have an effect on the performance of these molecules in a POC lateral flow system. Given that molecule size and structure contributes to the reaction kinetics of immunoassays, it is postulated that the largest DNA dendrimers, while having the most label moieties, might be kinetically disfavored in the lateral flow assay, while smaller dendrimers containing fewer labels might perform as well or better in the assay due to better reaction kinetics of the smaller molecules. As mentioned above, the largest dendrimer with ~1,440 biotin label moieties performed more poorly than the dendrimer with ~960 biotins. The ~1,440 biotin dendrimer contains about 81,500 DNA nucleotides, compared to about 69,900 DNA nucleotides for the ~960 biotin dendrimer, a 16.6% difference in total mass.

We believe this mass differential may be responsible for the difference in performance between these molecules, notwithstanding the higher number of biotin moieties on the larger dendrimer. Further, additional DNA dendrimers of other sizes have been tested and were found to generate higher or lower signal amplification results that were not directly proportional to the difference in sizes between the varying dendrimers.

EXAMPLE 4

Reduction of Non-Specific Binding (NSB) in a Direct Sandwich POC Lateral Flow Assay Materials required: as in Example 1, except different PBS buffers were utilized as described below.

Assay procedure (multi-step): the assay was performed as in Example 1 except that different PBS buffers were used as described below.

In order to reduce or eliminate non-specific binding from POC lateral flow assays which utilize DNA dendrimers, a buffer matrix was devised and tested. Nine phosphate buffered saline (PBS) buffers were tested, which consisted of varying percentages of bovine serum albumin (BSA, Sigma) or Tween-20 (Sigma).

The buffers were composed of:
1: 1×PBS, 0.1% BSA, 0.01% Tween-20
2: 1×PBS, 0.1% BSA, 0.1% Tween-20
3: 1×PBS, 0.1% BSA, 0.5% Tween-20
4: 1×PBS, 0.25% BSA, 0.01% Tween-20
5: 1×PBS, 0.25% BSA, 0.1% Tween-20
6: 1×PBS, 0.25% BSA, 0.5% Tween-20
7: 1×PBS, 0.5% BSA, 0.01% Tween-20
8: 1×PBS, 0.5% BSA, 0.1% Tween-20
9: 1×PBS, 0.5% BSA, 0.5% Tween-20

Results of Varying Buffers on NSB:

Lateral flow assays run in Buffer #7 resulted in the best specific signal and the lowest NSB. Unexpectedly, the presence of relatively high percentages of Tween-20 (>0.01%) in the PBS buffers resulted in an increase of NSB and those buffers were deselected for use in the lateral flow assays.

EXAMPLE 5

Enhancement of Sensitivity (Specific Signal) in a DNA Dendrimer Direct Sandwich POC Lateral Flow Assay by Addition of Specific Chemical Agents Prior studies have shown that various types of additive chemicals have an enhancing effect on the sensitivity (signal) produced when using DNA dendrimers in various assay systems (e.g., DNA/RNA microarrays). The chemicals used are typically of volume-excluding polymers such as polyethylene glycol (PEG) or other highly branched polysaccharide molecules. Two different lateral flow PBS buffer formulations: a) 1×PBS, 0.5% Tween-20 and b) 1×PBS, 0.5% BSA, and 0.01% Tween-20 (Buffer #7 from Example #4) were used for these experiments.

Materials required: as in Example 1, except the following chemicals were added to the DNA dendrimer dilution buffer at various concentrations:
PEG 3350
PEG 6000

PEG 8000
Ficoll (MW70,000)
Dextran sulfate
Sucrose

Assay procedure (multi-step): the assay was performed as in Example 1.

Results of Testing Enhancement Chemicals:

All chemicals were tested at various concentrations to determine if sensitivity was improved in an hCG titration assay (see Example 1), while also measuring NSB. Of the chemicals tested, dextran sulfate at a concentration of 0.75% (vol:vol) provided significant improvement of sensitivity, averaging 2-4 fold more sensitivity than the dextran sulfate free dendrimer assay, with no appreciable increase of NSB. The other chemical reagents provided little or no improvement of sensitivity or demonstrated unacceptable levels of NSB, or both, contrary to results achieved in other assay formats (e.g., ELISA).

EXAMPLE 6

Use of Different Types of Colloidal Gold Particles in a DNA Dendrimer POC Lateral Flow Assay Multiple sized streptavidin or neutravidin conjugated gold particles were tested in a direct sandwich POC lateral flow system with DNA dendrimers to ascertain which particles provided the most sensitivity with little or no NSB.

Materials required: as in Example 1, except the following gold particles were tested at an 1.0 OD final concentration:
Streptavidin-gold conjugate, 20 nm
Streptavidin-gold conjugate, 30 nm
Streptavidin-gold conjugate, 40 nm
Streptavidin-gold conjugate, 80 nm
Neutravidin-gold conjugate, 40 nm
Anti-biotin antibody-gold conjugate, 40 nm
Gold particles conjugated with DNA oligonucleotides complementary to DNA dendrimer sequences, 20 nm Results of Testing Various Gold Particles:

The best sensitivity, signal, and low NSB were achieved with both the 30 nm and 40 nm streptavidin-gold particles. Unexpectedly, the 80 nm streptavidin-gold particles produced a relatively weak signal, perhaps indicating a poorer ability of the larger particles to migrate effectively through the lateral flow membrane. The gold particles derivatized with the DNA oligonucleotides complementary to the DNA dendrimer worked well, achieving sensitivity equal to or exceeding the 20 nm streptavidin-gold particle (a larger oligonucleotide conjugated particle was not available, although we believe a larger particle would perform even better than the tested 20 nm particle).

EXAMPLE 7

Use of a DNA Dendrimer and Other Assay Components in a Partial or Fully Dried-Down, Direct or Indirect Sandwich POC Lateral Flow hCG Assay Materials required: as in Example 1 and Example 2, except for the following:
1. 3× Dry Down Solution (15% Trehalose (Fisher), 60% Sucrose (Sigma) solution, formulated in DDH$_2$O).
2. 37° C. forced air oven.
3. Glass test tubes (12×75 mm).

Drying-Down Reagent Preparation:
Anti-Mouse Antibody-Oligo Conjugate

The anti-mouse antibody-oligo conjugate was prepared at 1:18 dilution with a final concentration of 5% Trehalose and 20% Sucrose (starting with 3× Dry Down Solution diluted with 1×PBS with 0.5% BSA and 0.01% Tween-20).

DNA Dendrimer

A total mass of 65-200 ng of DNA dendrimer (per 5 uL per strip) was diluted in a final solution containing 5% Trehalose and 20% Sucrose (starting with 3× Dry Down Solution diluted with 1×PBS with 0.5% BSA and 0.01% Tween-20).

Streptavidin Colloidal Gold

Streptavidin-gold (SA-gold) conjugate was diluted to a concentration of 1.5 OD in 5% Trehalose and 20% Sucrose (starting with 3× Dry Down Solution diluted with 1×PBS with 0.5% BSA and 0.01% Tween-20).

Drying-Down Procedure:

Drying-Down a Single Reagent (Antibody-Oligo Conjugate, DNA Dendrimer, or SA-Gold):
1. Pipette 5 μl of properly prepared reagent onto the middle of the Porex conjugate pad on the lateral flow strip.
2. Place strips in 37° C. forced air oven for 30 minutes.

Drying-Down Two Reagents (Antibody-Oligo Conjugate or DNA Dendrimer):
1. Pipette 5 μl of the first reagent onto the Porex conjugate pad approximately 1 cm from the bottom of the pad on the lateral flow strip.
2. Pipette 5 μl of the second reagent onto the bottom of the Porex conjugate pad.
3. Place strips in 37° C. forced air oven for 30 minutes.

Drying-Down Three Reagents (Antibody-Oligonucleotide Conjugate, DNA Dendrimer, and SA-Gold):
1. Pipette 5 μl of the first reagent onto the Porex pad approximately 1 cm from the bottom of the pad.
2. Pipette 5 μl of the second reagent onto the middle of the Porex pad.
3. Pipette 5 μl of the third reagent onto the bottom of the Porex pad.
4. Place strips in 37° C. forced air oven for 30 minutes.

Assay Procedures:

A direct sandwich assay containing only one dried-down reagent:
1. Lateral flow strips were placed into glass tubes containing 65 μl of the appropriate amount of sample containing hCG antigen.
2. After the sample liquid was completely absorbed into the strip, the strips were moved to glass tubes containing 15 μl of either antibody-oligo conjugate or DNA dendrimer.
3. After all liquid was completely absorbed into the strips, the strips were moved into glass tubes containing 20 μl of SA-gold (providing the gold is not dried down on the strip).
4. After SA-gold conjugate was completely absorbed into the lateral flow strip, the strips were moved to glass tubes containing 35 μl of 1×PBS-TB buffer.
5. After completion of the assay, scores were recorded for as per the visual scoring guide.
6. The standard comparative assay substituted anti-hCG colloidal gold for SA-gold conjugate and did not require the use of the DNA dendrimer and antibody-oligo conjugate reagents.

A direct sandwich assay containing two dried-down reagents: Same procedure as immediately above, except that one of the "wet" reagent steps was eliminated, resulting in a two step assay.

A direct sandwich assay containing three dried-down reagents: Same procedure as immediately above, except that one of the "wet" reagent steps was eliminated, resulting in a one step assay.

Figure 7:
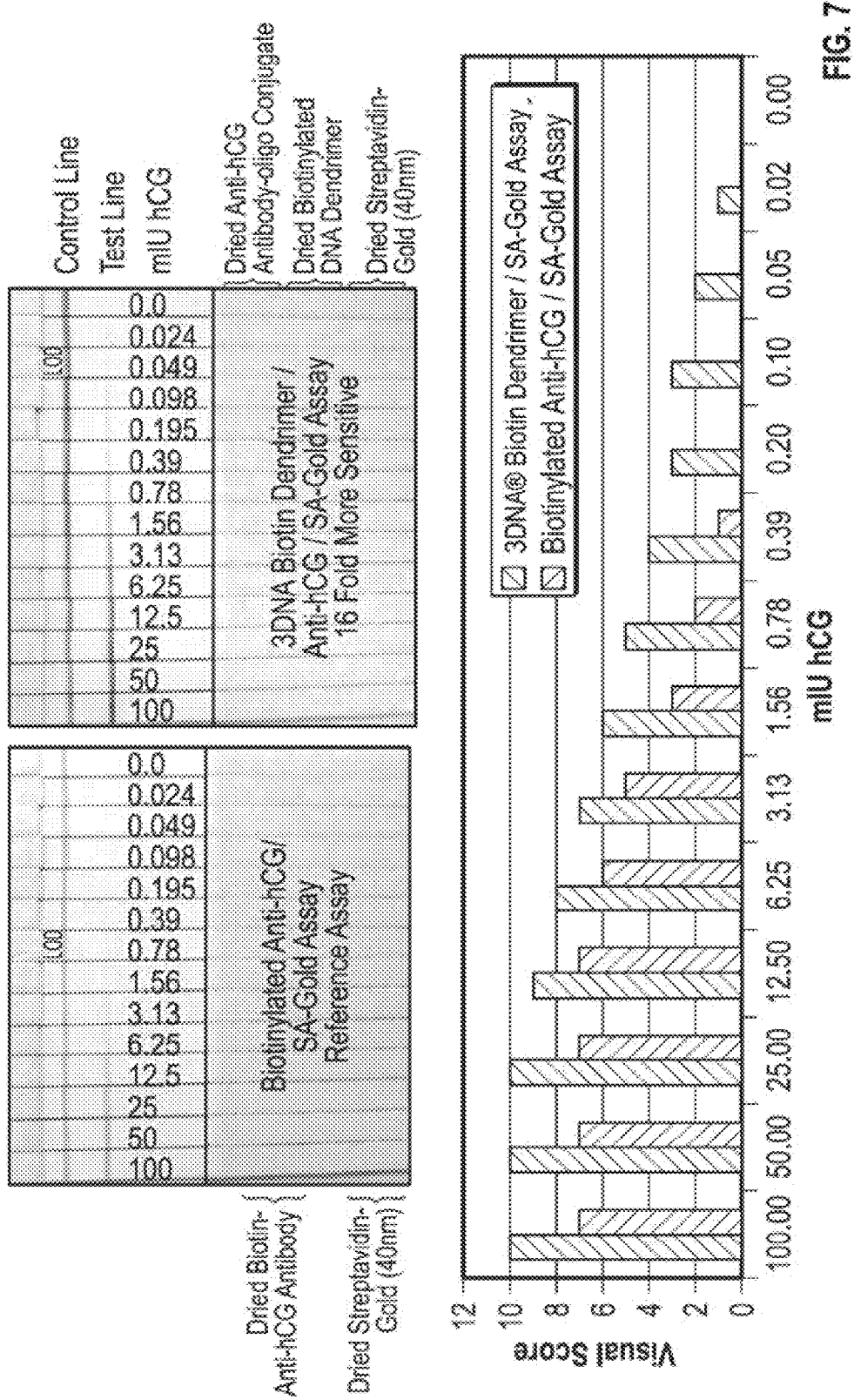
FIG. 7 illustrates conversion of the multistep Dendrimer LF assay to an exemplary 1-step fully dried down assay.

Results of Utilizing Dried Reagents (Including DNA Dendrimers) in a Direct Sandwich POC Lateral Flow hCG Assay After performing the above described assay on hCG samples that range from 100 mIU down to 0.024 mIU in two-fold serial dilutions, it was observed that a limit of detection (LOD) of 0.01-0.40 mIU hCG was achieved for the dendrimer assay, compared to a LOD of 3.1-6.2 mIU for the non-dendrimer standard hCG assay, resulting in a 8-64 fold improvement of sensitivity when using the DNA dendrimer as a signal amplifier (FIG. 7).

Indirect sandwich lateral flow assays containing up to four dried down reagents may also be performed in a manner similar to the above, with similar results.

EXAMPLE 8

Figure 8A:
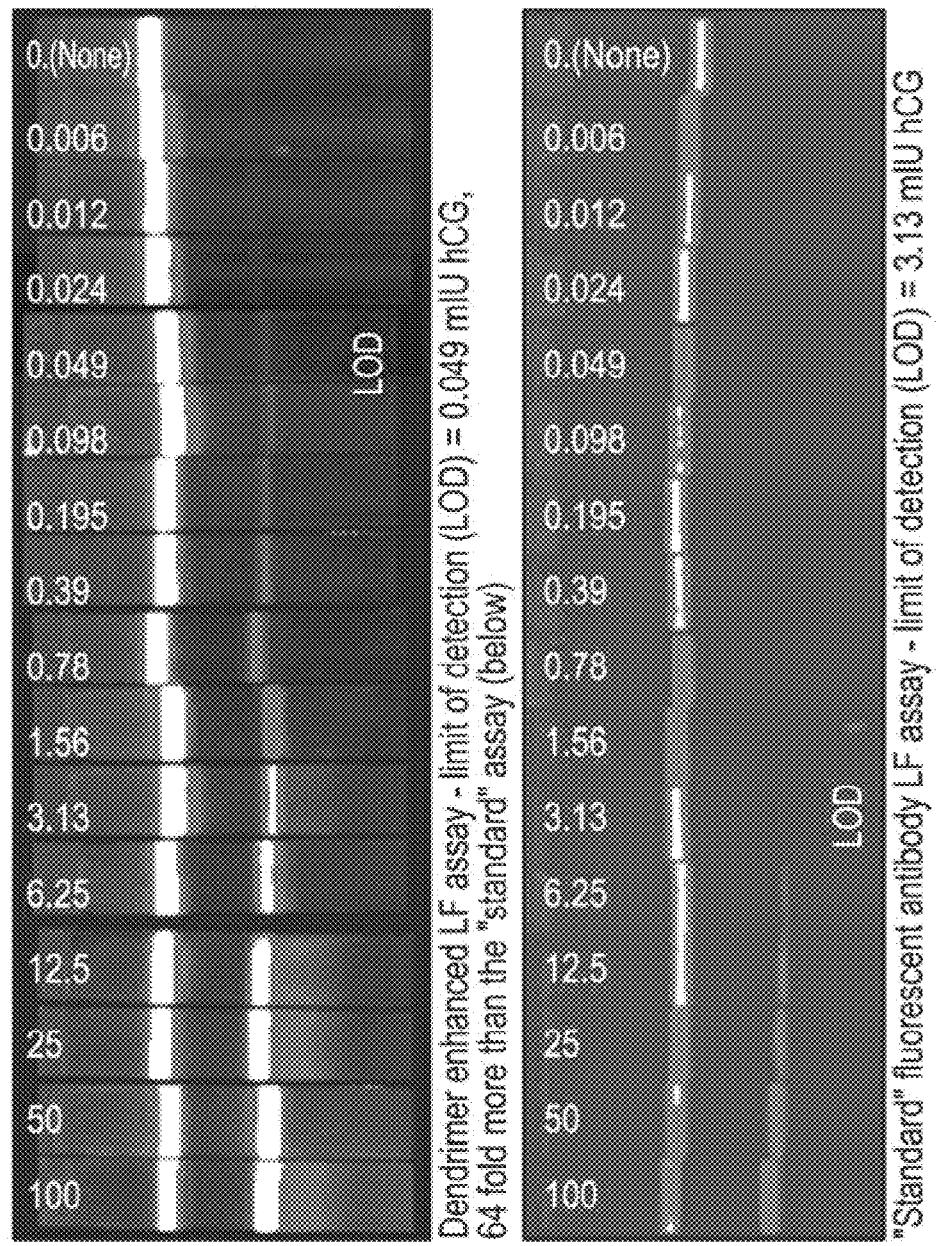
FIG. 8A illustrates lateral flow protein detection by exemplary fluorescent 3DNA Dendrimers: Comparison to directly labeled fluorescent antibody.
Figure 8B:
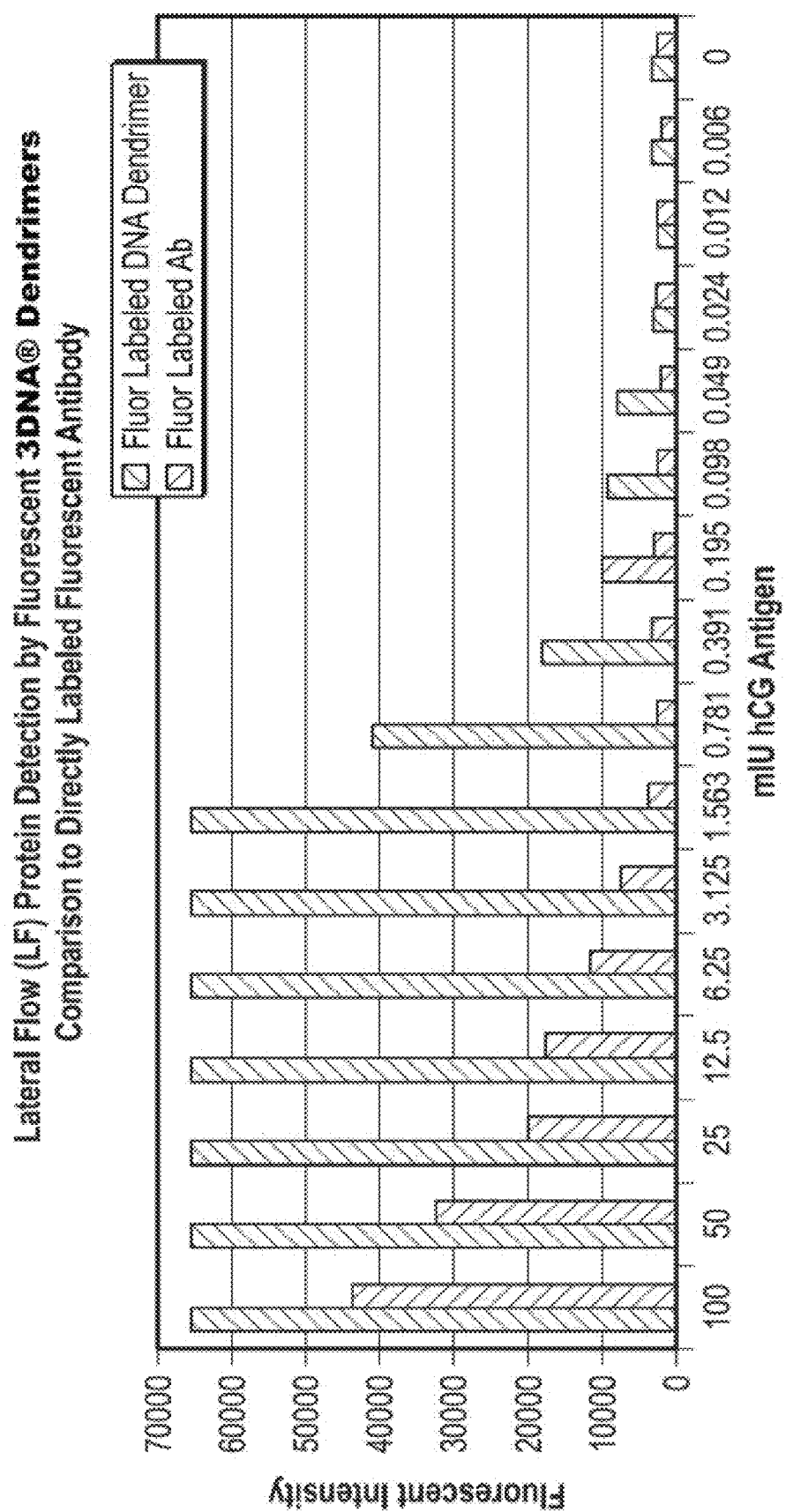
FIG. 8B illustrates lateral flow (LF) protein detection by exemplary fluorescent 3DNA Dendrimers: Comparison to directly labeled fluorescent antibody.

Use of a Fluorescent DNA Dendrimer and Other Assay Components in a Direct Sandwich POC Lateral Flow hCG Assay DNA dendrimers directly labeled with fluorescent dyes were used in POC lateral flow hCG assay ("wet"). The DNA dendrimer was directly labeled with ~960 fluorescent Oyster 650 dyes and was substituted for the biotinylated DNA dendrimer and SA-gold conjugate used in Example 1. Otherwise the assay was performed as described in Example 1. Results indicated that sensitivity was equal to or better than the sensitivity achieved using the SA-gold visible signal assay format (FIG. 8).

EXAMPLE 9

Use of a DNA Dendrimer and an Anti-hCG Mouse Monoclonal Targeting Antibody-Oligo Conjugate to Improve Sensitivity in an all Liquid ("Wet"), Direct Sandwich POC Lateral Flow Assay, where the DNA Dendrimer Contains Label Moieties Non-Covalently Bound This example is identical to Example 1, except for the following dendrimer manufacturing process describing the binding of labeled oligonucleotides and strand ligate to the dendrimer structure:

Add to a microfuge tube the following components:

| | |
|---|---|
| 4 layer DNA dendrimer | 1000 ng (1 ug) |
| strand ligate (from above) | 500 ng as strand (total synthesis 10uL) |
| c(+) 2x biotin oligo (35mer) (complementary to dendrimer "c arm" | 452.4 ng |
| N3(−) #1 2x biotin oligo (18mer) (complementary to "strand 3 ligate") | 291.9 ng |
| N3(−) #2 2x biotin oligo (19mer) (complementary to "strand 3 ligate") | 243.2 ng |
| N3(−) #3 2x biotin oligo (26mer) (complementary to "strand 3 ligate") | 316.2 ng |
| 5M NaCl | 1.1 uL (0.2M Final) |
| Nuclease free Water | to 28 uL total volume |

The above reactants are added together, mixed well, placed into a container of water at 75° C. and slow cooled to room temperature to allow for the hybridization of the strand ligate and labeled oligos to the dendrimer structure. Non-hybridized oligonucleotides are removed via the use of a size exclusion spin column or equivalent method.

Results for this example were consistent with the results reported in Example 1.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The claimed invention is:

1. A method for detecting an analyte in a liquid sample, which method comprises:
   a) contacting said liquid sample with a test device, wherein said test device comprises a porous matrix that comprises:
   1) a test zone on said porous matrix, said test zone comprising a test reagent that binds to an analyte, and
   2) a DNA dendrimer comprising a first component and a second component, wherein said first component is able to link said DNA dendrimer and a first binding reagent that binds to said analyte and said second component is able to link said DNA dendrimer to a detectable label, and wherein before said test device is contacted with said liquid sample, said DNA dendrimer, not linked to said first binding reagent, is dried on a location on said test device upstream from said test zone, wherein said DNA dendrimer is dried in the presence of a polysaccharide or a sugar or is air dried at 37° C., wherein a substance is dried on a portion of the test device upstream from the test zone, the dried substance is capable of being moved by a liquid sample and/or a further liquid to the test zone and/or a control zone to generate a detectable signal, the dried substance being the first binding reagent being linkable to the DNA dendrimer, and wherein said first binding reagent and said detectable label are dried on a portion of the test device upstream from the test zone; wherein said liquid sample flows laterally along said test device and passes said test zone to form a detectable signal to indicate presence, absence or amount of said analyte in said liquid sample, the formation of said detectable signal requires the use of said detectable label and said DNA dendrimer, said analyte is not a polynucleotide; and said liquid sample is applied to a site of said test device upstream of said test zone;
   b) transporting said analyte, if present in said liquid sample, said detectable label and said DNA dendrimer to said test zone to form a complex, wherein said complex comprises said test reagent, said analyte, said first binding reagent, said DNA dendrimer and said detectable label, both said test reagent and said first binding reagent bind to said analyte, said first binding reagent is linked to said DNA dendrimer through said first component and said detectable label is linked to said DNA dendrimer through said second component; and
   c) assessing the presence, absence, or amount of a signal generated by said detectable label at said test zone to determining the presence, absence or amount of said analyte in said liquid sample, wherein the method is conducted in a liquid comprising from about 0.001% (v/v) to about 0.01% (v/v) or less Polysorbate 20 and is conducted for detecting the analyte in a biological fluid.

2. The method of claim 1, which is conducted in a liquid comprising dextran sulfate.

3. The method of claim 1, wherein the first or second component is a polynucleotide.

4. The method of claim 1, wherein the analyte is a polypeptide or a small molecule, and the test reagent and/or the first binding reagent is an antibody that binds to the polypeptide or small molecule.

5. The method of claim 1, wherein the DNA dendrimer comprises from about 1 to about 324 said first components.

6. The method of claim 1, wherein the DNA dendrimer comprises from about 10 to about 1,500 the detectable label.

7. The method of claim 1, wherein the DNA dendrimer comprises from about 400 to about 80,000 DNA nucleotides.

8. The method of claim 1, wherein the DNA dendrimer comprises a one-layer, a two-layer, a three-layer or a four-layer structure.

* * * * *